US012805735B2

(12) United States Patent
Naito et al.

(10) Patent No.: US 12,805,735 B2
(45) Date of Patent: Nov. 24, 2026

(54) SPHYGMOMANOMETER

(71) Applicant: OMRON HEALTHCARE CO., LTD., Muko (JP)

(72) Inventors: Terumasa Naito, Kyoto (JP); Yukiya Sawanoi, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 750 days.

(21) Appl. No.: 18/119,606

(22) Filed: Mar. 9, 2023

(65) Prior Publication Data

US 2023/0210386 A1 Jul. 6, 2023

Related U.S. Application Data

(63) Continuation of application No. PCT/JP2021/038973, filed on Oct. 21, 2021.

(30) Foreign Application Priority Data

Nov. 4, 2020 (JP) ................................ 2020-184633

(51) Int. Cl.
*A61B 5/022* (2006.01)
*A61B 5/021* (2006.01)

(52) U.S. Cl.
CPC ...... *A61B 5/02208* (2013.01); *A61B 5/02141* (2013.01)

(58) Field of Classification Search
CPC ............ A61B 5/02208; A61B 5/02141; A61B 2505/07; A61B 2562/0204; A61B 5/02233; A61B 5/0225
See application file for complete search history.

(56) References Cited

U.S. PATENT DOCUMENTS 4,058,117 A * 11/1977 Kaspari .............. A61B 5/02233 600/495
4,889,132 A 12/1989 Hutcheson et al.
(Continued)

FOREIGN PATENT DOCUMENTS

JP S53-136385 A 11/1978
JP H03-097445 A 4/1991
(Continued)

OTHER PUBLICATIONS

Oct. 7, 2025 Office Action issued in Indian Patent Application No. 202317014778.

(Continued)

*Primary Examiner* — Justin Xu
(74) *Attorney, Agent, or Firm* — Oliff PLC

(57) ABSTRACT

A sphygmomanometer according to the present invention includes a blood pressure measuring cuff worn around a site to be measured, a pressure device that pressurizes or depressurizes the cuff, and a sound detection device that detects a sound generated by the site to be measured via the cuff. An amplification factor setting unit measures a first passage time required for the pressure of the cuff to pass through a first pressure range in a pressurization process of the cuff, and variably sets an amplification factor for a Korotkoff sound component according to the first passage time. A blood pressure calculation unit receives an output of the sound detection device according to the sound from the cuff, amplifies the Korotkoff sound component included in the output at a set amplification factor, and calculates a blood pressure of the site to be measured.

4 Claims, 15 Drawing Sheets

(56) References Cited

U.S. PATENT DOCUMENTS

| | | | | |
|---|---|---|---|---|
| 5,406,953 | A | 4/1995 | Bui | |
| 2011/0015531 | A1* | 1/2011 | Fujii | A61B 5/0225 600/493 |
| 2011/0295130 | A1* | 12/2011 | Tokko | A61B 5/02141 600/494 |
| 2018/0235488 | A1* | 8/2018 | Aelen | A61B 5/02225 |

FOREIGN PATENT DOCUMENTS

| | | | |
|---|---|---|---|
| JP | H05-317270 | A | 12/1993 |
| JP | 2000-107143 | A | 4/2000 |
| JP | 2012-065806 | A | 4/2012 |
| JP | 5408142 | B2 | 2/2014 |

OTHER PUBLICATIONS

Nov. 30, 2021 International Search Report issued in International Patent Application No. PCT/JP2021/038973.

Apr. 9, 2026 Office Action issued in Indian Patent Application No. 202317014778.

Orbit-K Blood Pressure Cuff; < https://www.suntechmed.com/bp-products/stress-test-blood-pressure-monitors/orbit-k-blood-pressure-cuff#features;> (Aug. 21, 2019).

* cited by examiner

SPHYGMOMANOMETER

CROSS-REFERENCE TO RELATED APPLICATION

This is a continuation application of International Application No. PCT/JP2021/038973, with an International filing date of Oct. 21, 2021, which claims priority of Japanese Patent Application No. 2020-184633 filed on Nov. 4, 2020, the entire content of which is hereby incorporated by reference.

TECHNICAL FIELD

The present invention relates to a sphygmomanometer, and more particularly to a sphygmomanometer that measures a blood pressure based on a Korotkoff sound by compressing a site to be measured.

BACKGROUND ART

Conventionally, as this type of sphygmomanometer, for example, as disclosed in Patent Literature 1 (JP S53-136385 A), a technique is known in which an amplification factor of an amplifier is varied so that an amplitude of a Korotkoff sound detected for each beat becomes constant in a depressurization process of a cuff (manchette). Thus, it is designed to be able to recognize Korotkoff sounds reliably. Furthermore, as disclosed in Patent Literature 2 (JP H05-317270 A), a technique of variably setting a K sound recognition level (A signal exceeding the K sound recognition level is treated as a Korotkoff sound.) on the basis of a depressurization speed in a depressurization process of a cuff is known. As a result, it is designed to be able to stably recognize the Korotkoff sound.

SUMMARY OF INVENTION

By the way, in a case where a site to be measured is a thick arm (with a large peripheral length), since there are many biological tissues between an artery and a body surface, it is difficult to transmit a sound, and a Korotkoff sound level tends to be low. Meanwhile, in a case where the site to be measured is a thin arm (with a small peripheral length), since there are few biological tissues between the artery and the body surface, the Korotkoff sound level tends to be high. Therefore, if the amplification factor is set large on the basis of the Korotkoff sound level in a case where the site to be measured is a thick arm, there is a problem that a signal amplified with the amplification factor is saturated (That is, the amplified signal exceeds an input range of a processor that processes the signal.) in a case where the site to be measured is a thin arm. As a result, the accuracy of the blood pressure measurement decreases. The above Patent Literatures 1 and 2 do not have such a problem awareness, and the techniques of the above Patent Literatures 1 and 2 do not solve the above problem.

Therefore, an object of the present invention is to provide a sphygmomanometer capable of reducing or eliminating the change of a Korotkoff sound level depending on a peripheral length of a site to be measured and capable of accurately measuring a blood pressure.

In order to solve the above-mentioned problem, a sphygmomanometer that measures a blood pressure by a Korotkoff sound generated by a site to be measured, the sphygmomanometer of the present disclosure comprises:

- a blood pressure measuring cuff worn around the site to be measured;
- a pressure device that supplies a fluid to the blood pressure measuring cuff to pressurize the blood pressure measuring cuff, or discharges a fluid from the blood pressure measuring cuff to depressurize the blood pressure measuring cuff;
- a sound detection device that detects a sound generated by the site to be measured via the blood pressure measuring cuff;
- an amplification factor setting unit that measures a first passage time required for pressure of the blood pressure measuring cuff to pass through a predetermined first pressure range in a pressurization process of the blood pressure measuring cuff by the pressure device, and variably sets an amplification factor for a Korotkoff sound component according to the first passage time; and
- a blood pressure calculation unit that receives an output of the sound detection device according to the sound from the blood pressure measuring cuff, amplifies a Korotkoff sound component included in the output with an amplification factor set by the amplification factor setting unit, and calculates a blood pressure of the site to be measured based on the amplified Korotkoff sound component in the pressurization process or a depressurization process subsequent to the pressurization process.

In the present specification, the "site to be measured" includes an upper limb such as an upper arm and a wrist or a lower limb such as an ankle, and typically refers to a rod-like site.

The "blood pressure measuring cuff" typically includes a fluid bag (This is referred to as "pressing fluid bag".) for compressing the site to be measured.

The "pressure device" typically includes a pump and a valve.

The "sound detection device" typically includes a microphone.

The "predetermined first pressure range" refers to, for example, a range of 25 mmHg to 35 mmHg.

In another aspect, a sphygmomanometer that measures a blood pressure by a Korotkoff sound generated by a site to be measured, the sphygmomanometer of the present disclosure comprises:

- a blood pressure measuring cuff worn around the site to be measured;
- a pressure device that supplies a fluid to the blood pressure measuring cuff to pressurize the blood pressure measuring cuff, or discharges a fluid from the blood pressure measuring cuff to depressurize the blood pressure measuring cuff;
- a sound detection device that detects a sound generated by the site to be measured via the blood pressure measuring cuff;
- an input unit that inputs size information indicating which cuff size the currently connected blood pressure measuring cuff has among a plurality of types of cuff sizes prepared in advance;
- an amplification factor setting unit that variably sets an amplification factor for a Korotkoff sound component according to the size information input by the input unit; and
- a blood pressure calculation unit that receives an output of the sound detection device according to the sound from the blood pressure measuring cuff, amplifies a Korotkoff sound component included in the output with an amplification factor set by the amplification factor setting unit, and calculates a blood pressure of the site to be measured based on the amplified Korotkoff sound component in a pressurization process or a depressurization process by the pressure device.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, embodiments of the present invention will be described in detail with reference to the drawings.

(Schematic Configuration of Sphygmomanometer)

Figure 1:
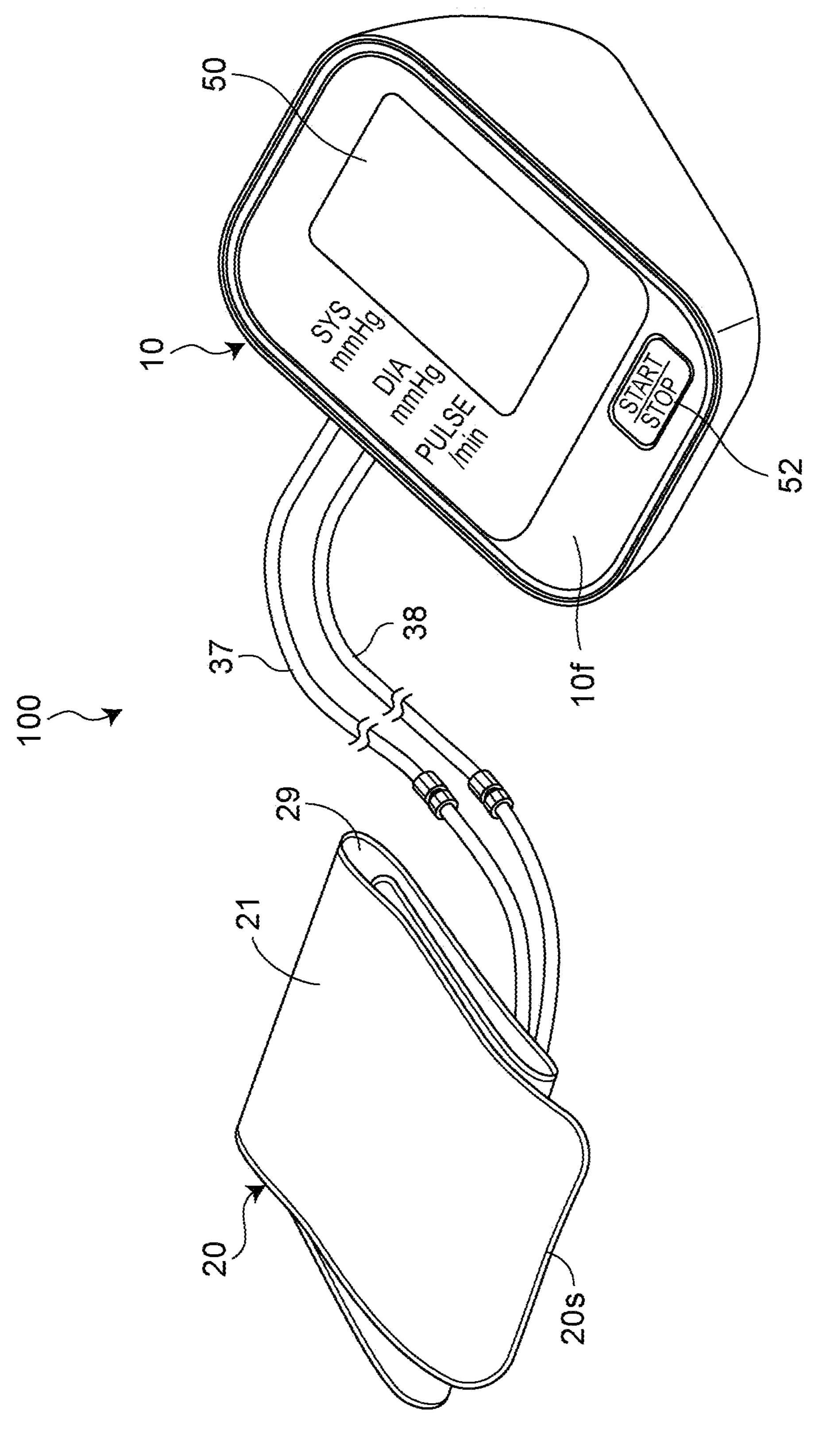
FIG. 1 is a diagram illustrating an appearance of a sphygmomanometer according to an embodiment of the present invention.

FIG. 1 illustrates an appearance of a sphygmomanometer 100 according to an embodiment of the present invention. The sphygmomanometer 100 roughly includes a blood pressure measuring cuff 20 worn around a rod-shaped site 90 to be measured (see FIG. 4A) such as an upper arm or a wrist, and a main body 10 connected to the cuff 20 so as to be capable of flowing a fluid through an air pipe 38 as a first fluid pipe and an air pipe 37 as a second fluid pipe.

(Configuration of Blood Pressure Measuring Cuff)

As can be seen from FIG. 1, the cuff 20 is configured by making an outer cloth 21 having an elongated strip shape (in this example, a rounded rectangle) and an inner cloth 29 having a shape corresponding to the outer cloth 21 face each other, and sewing (or welding) peripheral edge parts 20*s* of the outer cloth 21 and the inner cloth 29.

Figure 3A:
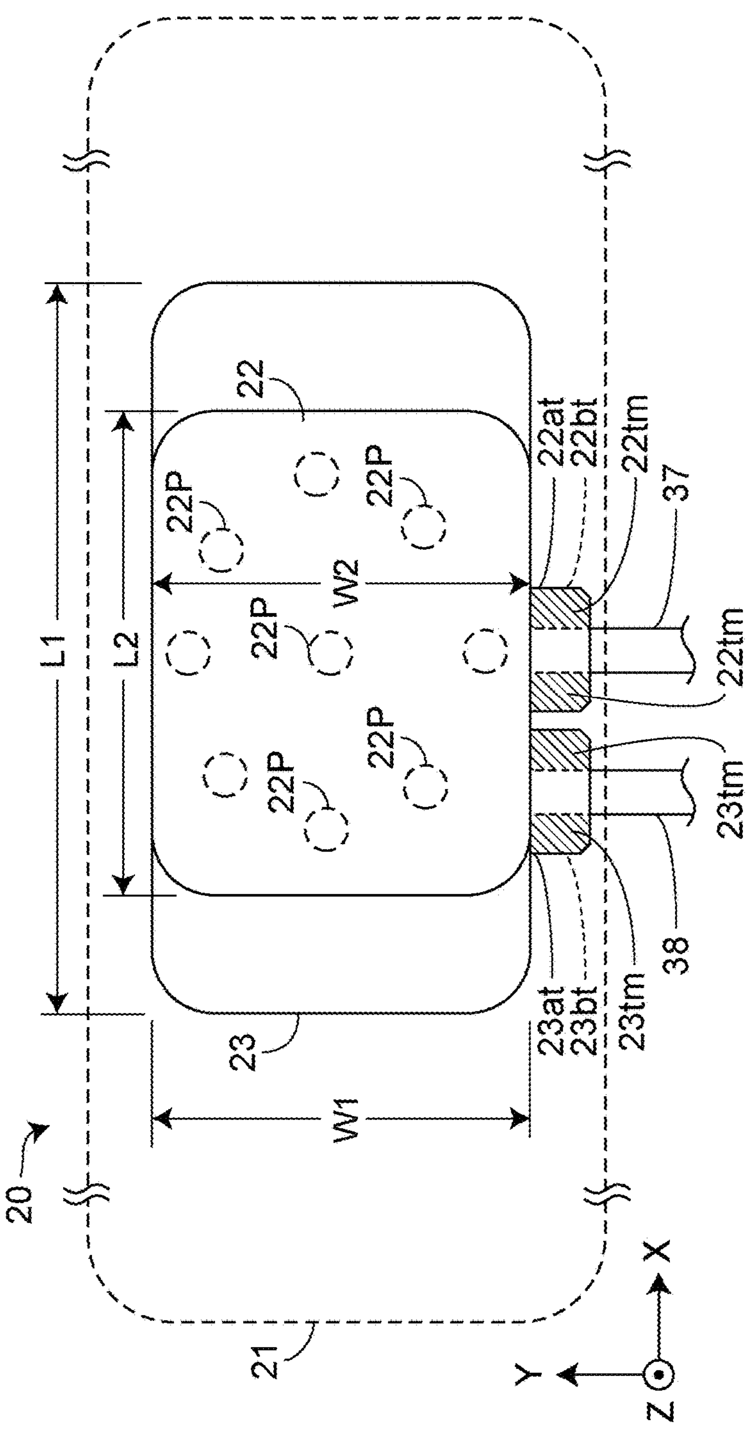
FIG. 3A is a diagram schematically illustrating a planar layout of a sound acquisition fluid bag and a pressing fluid bag included in a blood pressure measuring cuff in a state where the blood pressure measuring cuff included in the sphygmomanometer is unfolded.
Figure 3B:
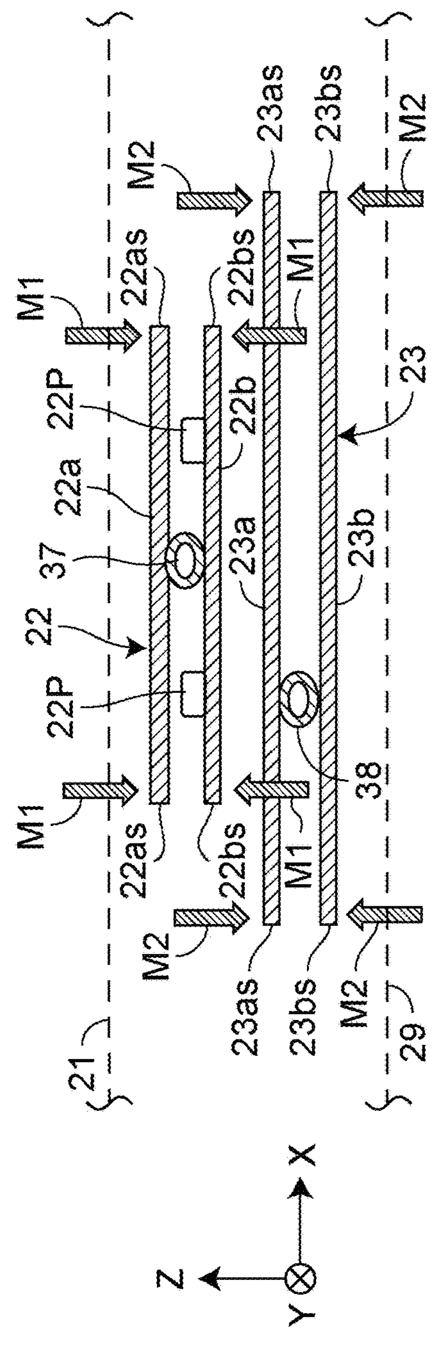
FIG. 3(B) is a diagram schematically illustrating cross sections of the sound acquisition fluid bag and the pressing fluid bag in an exploded state.

FIG. 3A schematically illustrates a planar layout of a sound acquisition fluid bag 22 and a pressing fluid bag 23 included in the cuff 20 in a state where the cuff 20 is unfolded. FIG. 3B schematically illustrates cross sections of the sound acquisition fluid bag 22 and the pressing fluid bag 23 in an exploded state. Here, regarding the cuff 20, a longitudinal direction X means a direction in which the outer cloth 21 extends in a band shape, and corresponds to a circumferential direction surrounding the site 90 to be measured in a worn state (see FIG. 4A). A width direction Y means a direction perpendicular to the longitudinal direction X in a plane along the outer cloth 21, and corresponds to a direction in which an artery 91 passes through the site 90 to be measured in the worn state. Furthermore, a thickness direction Z means a direction perpendicular to both the longitudinal direction X and the width direction Y (that is, outer cloth 21), and corresponds to a direction perpendicular to an outer peripheral surface of the site 90 to be measured in the worn state.

As can be seen from FIG. 3B, in this example, the cuff 20 includes the pressing fluid bag 23 and the sound acquisition fluid bag 22 configured separately from the pressing fluid bag 23 between the inner cloth 29 and the outer cloth 21. The pressing fluid bag 23 is provided on a side of the inner cloth 29 mainly to compress the site 90 to be measured. The sound acquisition fluid bag 22 is provided between the outer cloth 21 and the pressing fluid bag 23 in order to acquire a sound from the site 90 to be measured via the pressing fluid bag 23. In this example, the sound acquisition fluid bag 22 is partially bonded to the pressing fluid bag 23 so as not to be displaced with respect to the pressing fluid bag 23. The pressing fluid bag 23 is partially bonded to the outer cloth 21 so as not to be displaced with respect to the outer cloth 21.

As can be seen from FIG. 3A, the pressing fluid bag 23 has a substantially rectangular shape with rounded corners extending along the longitudinal direction X in a plane along the outer cloth 21. The sound acquisition fluid bag 22 has a substantially rectangular shape with round corners smaller than those of the pressing fluid bag 23 in a plane along the outer cloth 21.

As can be seen from FIG. 3B, the pressing fluid bag 23 includes a pair of sheets 23*a* and 23*b* facing each other in the thickness direction Z, and peripheral edge parts 23*as* and 23*bs* of the pair of sheets 23*a* and 23*b* are annularly joined (in this example, welded) to each other as indicated by arrows M2 to form a bag shape. The sound acquisition fluid bag 22 includes a pair of sheets 22*a* and 22*b* facing each other in the thickness direction Z, and peripheral edge parts 22*as* and 22*bs* of the pair of sheets 22*a* and 22*b* are annularly joined to each other as indicated by arrows M1 to form a bag shape. In this example, the sheets 23*a*, 23*b*, 22*a*, and 22*b* are made of polyurethane resin.

The pair of sheets 23*a* and 23*b* constituting the pressing fluid bag 23 has substantially rectangular tabs 23*at* and 23*bt* protruding in the width direction (−Y direction) in FIG. 3A at positions corresponding to each other. In a state where the air pipe 38 is sandwiched between the tabs 23*at* and 23*bt*, parts 23*tm* and 23*tm* (indicated by hatching) of the tabs 23*at* and 23*bt* corresponding to both sides of the air pipe 38 are entirely welded, so that the air pipe 38 is connected to the pressing fluid bag 23 so as to be capable of flowing a fluid. The pressing fluid bag 23 can be expanded by being supplied with air through the air pipe 38 and can be contracted by being discharged with air. Similarly, the pair of sheets 22*a* and 22*b* constituting the sound acquisition fluid bag 22 has substantially rectangular tabs 22*at* and 22*bt* protruding in the width direction (−Y direction) in FIG. 3A at positions corresponding to each other. The air pipe 37 is connected to the sound acquisition fluid bag 22 so as to be capable of flowing a fluid by entirely welding parts 22*tm* and 22*tm* (indicated by hatching) of the tabs 22*at* and 22*bt* corresponding to both sides of the air pipe 37 with the air pipe 37 interposed between the tabs 22*at* and 22*bt*. A sound acquired by the sound acquisition fluid bag 22 is transmitted to the main body 10 through the air pipe 37 (Details will be described later.).

A plurality of protrusions 22*p*, 22*p*, . . . as spacers are provided in a gap between the pair of sheets 22*a* and 22*b* facing each other and forming the sound acquisition fluid bag 22. In this example, the protrusions 22*p*, 22*p*, . . . each have a short columnar shape, and are integrally formed with the sheet 22*b* disposed on a side of the pressing fluid bag 23. Thus, the spacers can be easily configured. In this example, these protrusions 22*p*, 22*p*, . . . are dispersedly arranged at substantially equal intervals in a plane (XY plane) along the outer cloth 21. This prevents the pair of sheets 22*a* and 22*b* from coming into close contact with each other during blood pressure measurement. Therefore, the sound acquisition fluid bag 22 can stably acquire the sound from the site 90 to be measured via the pressing fluid bag 23. As a result, the Korotkoff sound can be stably acquired.

The outer cloth 21 can be curved or bent, but is configured not to substantially expand and contract in order to restrict the entire expansion of the sound acquisition fluid bag 22 and the pressing fluid bag 23 in a direction away from the site 90 to be measured at the time of blood pressure measurement. On the other hand, the inner cloth 29 can be curved or is bendable, and is easily stretchable so that the pressing fluid bag 23 easily compresses the site 90 to be measured during blood pressure measurement. Here, the outer cloth 21 and the inner cloth 29 are not limited to those knitted, and may be made of one layer or a plurality of layers of resin. Dimensions of the outer cloth 21 and the inner cloth 29 in the longitudinal direction X are set to be longer than a peripheral length of the site 90 to be measured (in this example, an upper arm). Dimensions of the outer cloth 21 and the inner cloth 29 in the width direction Y are set to be slightly larger than dimensions of the pressing fluid bag 23 (and the sound acquisition fluid bag 22) in the width direction Y.

In the sphygmomanometer 100 including the cuff 20, the sound acquisition fluid bag 22 acquires the sound from the site 90 to be measured via the pressing fluid bag 23. In the worn state, the pressing fluid bag 23 extends along the circumferential direction of the site 90 to be measured. Therefore, even if a position (in particular, a circumferential position) where the cuff 20 (pressing fluid bag 23) is worn with respect to the site 90 to be measured varies, the influence on a level of the sound entering the pressing fluid bag 23 from the artery 91 passing through the site 90 to be measured is small, and as a result, the sound collection by the sound acquisition fluid bag 22 is stabilized. Therefore, the K sound signal Ks representing the Korotkoff sound can be stably acquired.

(Setting of Plane-Direction Dimensions of Pressing Fluid Bag and Sound Acquisition Fluid Bag)

The plane-direction dimensions of the pressing fluid bag 23 and the sound acquisition fluid bag 22 are set according to a cuff size (is set as a specification of the cuff, and defines plane-direction dimensions of the outer cloth 21 and the inner cloth 29.). For example, as the cuff size, L (large), M (medium), and S (small) are set for the upper arm as illustrated in a "cuff size" field of Table 1 below.

TABLE 1

| | Pressing fluid bag | | Sound acquisition fluid bag | |
|---|---|---|---|---|
| Cuff size | L1 [mm] | W1 [mm] | L2 [mm] | W2 [mm] |
| L (large) | 312.5 | 150.0 | 78.1-312.5 | 75-150 |
| M (middle) | 235.0 | 125.0 | 58.8-235 | 62.5-125 |
| S (small) | 167.0 | 90.0 | 41.8-167 | 45-90 |

The dimension L1 in the longitudinal direction X and the dimension W1 in the width direction Y of the pressing fluid bag 23 illustrated in FIG. 3A are variably set as shown in a "pressing fluid bag" column of Table 1 according to the cuff size corresponding to an arm circumference of the subject (the peripheral length of the site 90 to be measured). That is, for the cuff size L (large) for the upper arm, the dimension L1 in the longitudinal direction X is set to 312.5 mm, and the dimension W1 in the width direction Y is set to 150.0 mm. For the cuff size M (middle) for the upper arm, the dimension L1 in the longitudinal direction X is set to 235.0 mm, and the dimension W1 in the width direction Y is set to 125.0 mm. For the cuff size S (small) for the upper arm, the dimension L1 in the longitudinal direction X is set to 167.0 mm, and the dimension W1 in the width direction Y is set to 90.0 mm. Due to the setting of the plane-direction dimensions L1 and W1 of the pressing fluid bag 23, the cuff 20 can be fitted and worn to subjects of various arm circumferences and wrist circumferences. Similarly, the dimension L2 in the longitudinal direction X and the dimension W2 in the width direction Y of the sound acquisition fluid bag 22 are variably set as shown in a "sound acquisition fluid bag" column of Table 1 according to the cuff size corresponding to the arm circumference of the subject. Note that the cuffs 20 having the cuff sizes L (large), M (medium), and S (small) are referred to as "L cuff", "M cuff", and "S cuff", respectively.

(Configuration of Main Body)

Figure 2:
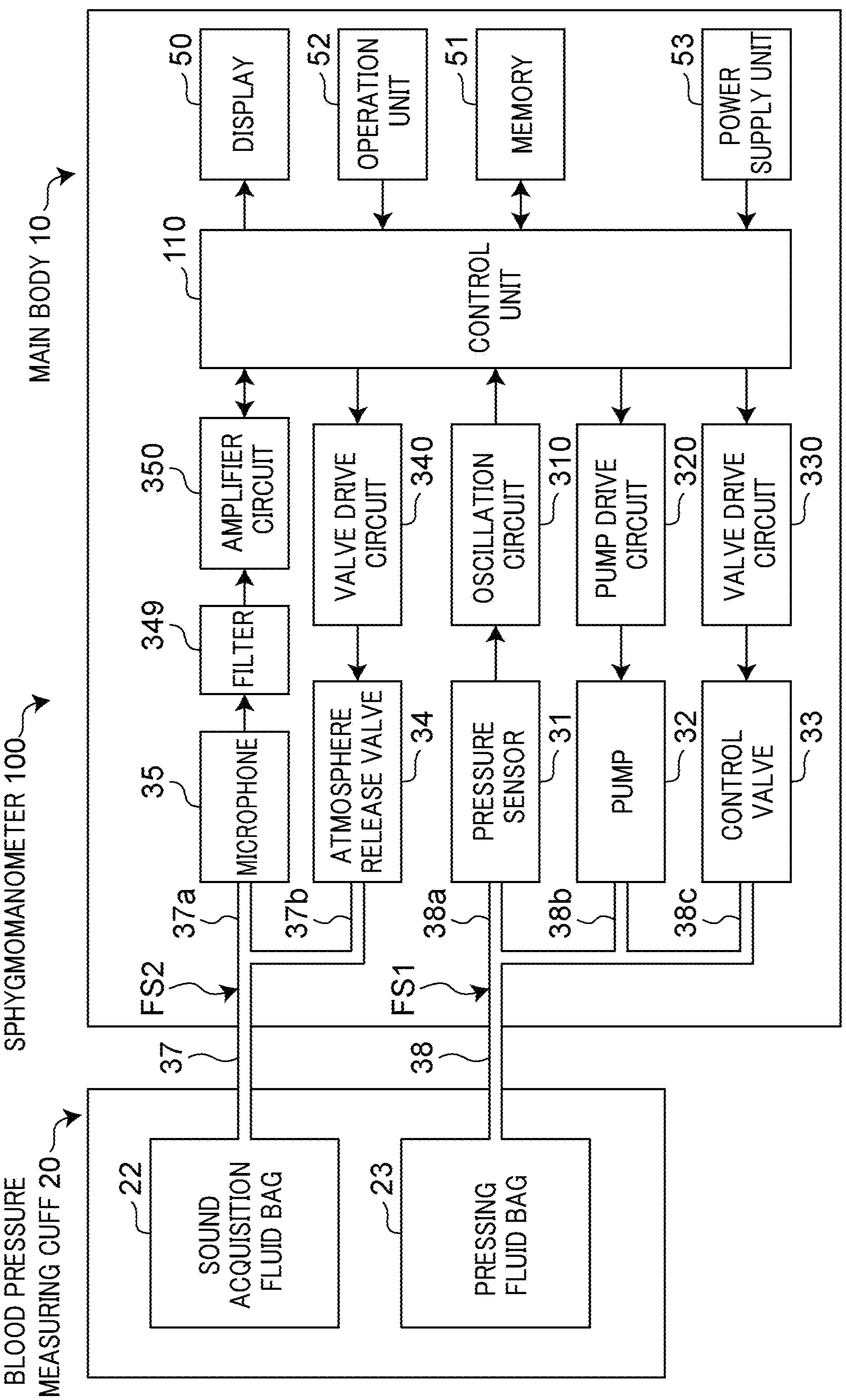
FIG. 2 is a diagram illustrating a block configuration of the sphygmomanometer.

As illustrated in FIG. 2, the main body 10 includes a control unit 110, a display 50, an operation unit 52, a memory 51 as a storage unit, a power supply unit 53, a pressure sensor 31, an oscillation circuit 310, a pump 32 and a control valve 33 as a pressure device, a pump drive circuit 320, a valve drive circuit 330, a microphone 35 as a sound detection device, a filter 349, an amplifier circuit 350, an atmosphere release valve 34, and a valve drive circuit 340. In this example, an air pipe 38*a* connected to the pressure sensor 31, an air pipe 38*b* connected to the pump 32, and an air pipe 38*c* connected to the control valve 33 join to form one air pipe 38 connected to the pressing fluid bag 23 so as to be capable of flowing a fluid. The air pipe 38 as the first fluid pipe is a generic term including these air pipes 38*a*, 38*b*, and 38*c*. Furthermore, an air pipe 37*a* connected to the microphone 35 and an air pipe 37*b* connected to the atmosphere release valve 34 join to form one air pipe 37 connected to the sound acquisition fluid bag 22 so as to be capable of flowing a fluid. The air pipe 37 as the second fluid pipe is a generic term including these air pipes 37*a* and 37*b*.

As illustrated in FIG. 1, the display 50 and the operation unit 52 are disposed on a front panel 10*f* of the main body 10. In this example, the display 50 includes a liquid crystal display (LCD), and displays predetermined information in accordance with a control signal from the control unit 110. In this example, a systolic blood pressure (SYS, units; mmHg), a diastolic blood pressure (DIA, units; mmHg), and a pulse rate PULSE (unit; beat/min) are displayed. Note that the display 50 may be an organic electro luminescence (EL) display, or may include a light emitting diode (LED).

In this example, the operation unit 52 includes a measurement switch (for simplicity, denoted by the same reference sign 52) for receiving an instruction to start/stop the measurement of a blood pressure, and inputs an operation signal according to an instruction of the user to the control unit 110. Specifically, when the measurement switch 52 is pressed, an operation signal indicating that blood pressure measurement should be started is input to the control unit 110, and the control unit 110 starts blood pressure measurement described later (When the blood pressure measurement is completed, the operation is automatically stopped.). When the measurement switch 52 is pressed during the execution of the blood pressure measurement, the control unit 110 urgently stops the blood pressure measurement.

The memory 51 illustrated in FIG. 2 stores data of a program for controlling the sphygmomanometer 100, setting data for setting various functions of the sphygmomanometer 100, data of a measurement result of a blood pressure value, and the like. Furthermore, the memory 51 is used as a work memory or the like when the program is executed.

The control unit 110 includes a central processing unit (CPU) as a processor, and controls the entire operation of the sphygmomanometer 100. Specifically, the control unit 110 acts as a pressure control unit according to a program for controlling the sphygmomanometer 100 stored in the memory 51, and performs control to drive the pump 32 and the control valve 33 as a pressure device according to an operation signal from the operation unit 52. Furthermore, the control unit 110 works as a blood pressure calculation unit together with the amplifier circuit 350, calculates a blood pressure value based on the output of the microphone 35, and controls the display 50 and the memory 51. A specific method of the blood pressure measurement will be described later.

The pressure sensor 31 is a piezoresistive pressure sensor in this example, and outputs the pressure (This is referred to as "cuff pressure Pc".) of the pressing fluid bag 23 contained in the cuff 20 as an electric resistance due to the piezoresistive effect through the air pipe 38. The oscillation circuit 310 oscillates at an oscillation frequency corresponding to the electric resistance from the pressure sensor 31. The control unit 110 obtains the cuff pressure Pc according to the oscillation frequency.

The pump 32 is driven by the pump drive circuit 320 based on a control signal given from the control unit 110, and supplies air to the pressing fluid bag 23 included in the cuff 20 through the air pipe 38. As a result, the pressure (cuff pressure Pc) of the pressing fluid bag 23 is pressurized.

The control valve 33 includes a normally-open type electromagnetic control valve, is driven by the valve drive circuit 330 based on a control signal given from the control unit 110, and is opened and closed to control the cuff pressure by discharging or enclosing the air in the pressing fluid bag 23 through the air pipe 38.

The microphone 35 detects a sound acquired by the sound acquisition fluid bag 22 through the air pipe 37, and outputs an electric signal according to the sound. In this example, the filter 349 performs filtering, including a fast Fourier transform (FFT), on the electric signal output by the microphone 35 to extract a K sound signal (represented by Ks) representing a Korotkoff sound. As illustrated in FIG. 4B, the K sound signal (Korotkoff sound component) Ks is typically obtained as a pulse-like signal oscillating at a high level and a low level with respect to a reference level ba. In FIG. 4B, an amplitude of a peak-to-peak of the K sound signal Ks is represented by Ap-p. The amplifier circuit 350 amplifies the K sound signal Ks output from the filter 349 with a variably set amplification factor α. Based on the amplified K sound signal (This is defined as αKs.), the control unit 110 calculates a blood pressure of the site 90 to be measured (Details will be described later.).

The atmosphere release valve 34 illustrated in FIG. 2 is a normally-open type electromagnetic control valve, is driven by the valve drive circuit 340 based on a control signal given from the control unit 110, and is opened and closed to open or seal a second fluid system FS2 including the sound acquisition fluid bag 22 and the air pipe 37 to the atmosphere.

In this example, a first fluid system FS1 including the pressing fluid bag 23, the air pipe 38, the pressure sensor 31, the pump 32, and the control valve 33, and the second fluid system FS2 including the sound acquisition fluid bag 22, the air pipe 37, the microphone 35, and the atmosphere release valve 34 are separated from each other so as not to be capable of flowing a fluid, and the separation is maintained also in the main body 10. As a result, it is possible to prevent the pulse sound (pulse wave sound) from being mixed from the first fluid system FS1 with respect to the sound (including a Korotkoff sound component) passing through the second fluid system FS2 (in particular, the air pipe 37). Therefore, the Korotkoff sound can be stably acquired.

The power supply unit 53 supplies power to the control unit 110, the display 50, the memory 51, the pressure sensor 31, the pump 32, the control valve 33, the microphone 35, the atmosphere release valve 34, and other units in the main body 10.

(Mode of Wearing Blood Pressure Measuring Cuff)

Figure 4A:
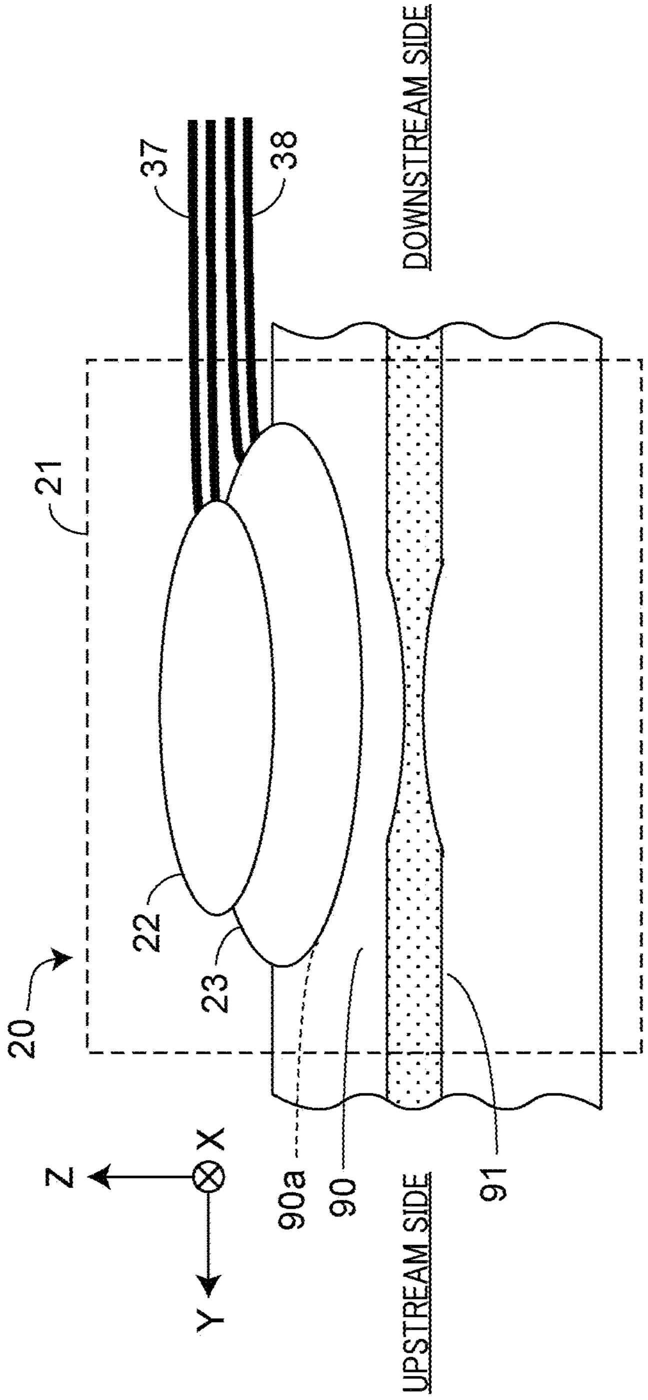
FIG. 4A is a diagram schematically illustrating a mode in which the cuff is worn around an outer periphery of an upper arm as a site to be measured.
Figure 4B:
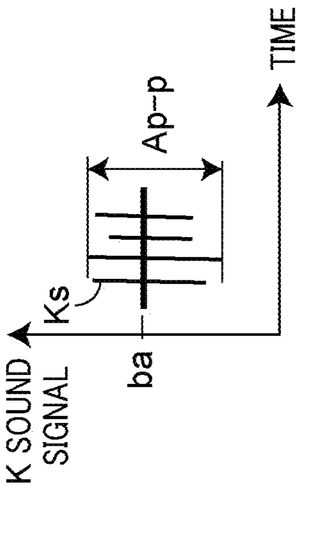
FIG. 4B is a diagram schematically illustrating a K sound signal (representing a Korotkoff sound) acquired using a sound detection device (microphone) through the sound acquisition fluid bag.

As illustrated in FIG. 4A (a cross section along the artery 91 passing through the site 90 to be measured), the cuff 20 is worn in a mode in which the longitudinal direction X of the cuff 20 surrounds the outer peripheral surface of the site 90 to be measured (in this example, the upper arm). At the time of wearing, the outer cloth 21 is fixed by a hook-and-loop fastener (not illustrated) so as not to be loosened. Note that, in FIG. 4A, the inner cloth 29 is not illustrated for simplicity, and the pressing fluid bag 23 and the sound acquisition fluid bag 22 are each drawn in an elliptical shape. In this worn state, the inner cloth 29 not illustrated in the drawing, the pressing fluid bag 23, the sound acquisition fluid bag 22, and the outer cloth 21 are arranged in this order in the thickness direction Z with respect to the outer peripheral surface of the site 90 to be measured. Note that, in the worn state, since the air pipes 37 and 38 extend toward a downstream side (−Y direction) of a blood flow passing through the artery 91, the air pipes 37 and 38 do not interfere with the wearing.

(Blood Pressure Measurement)

Figure 5:
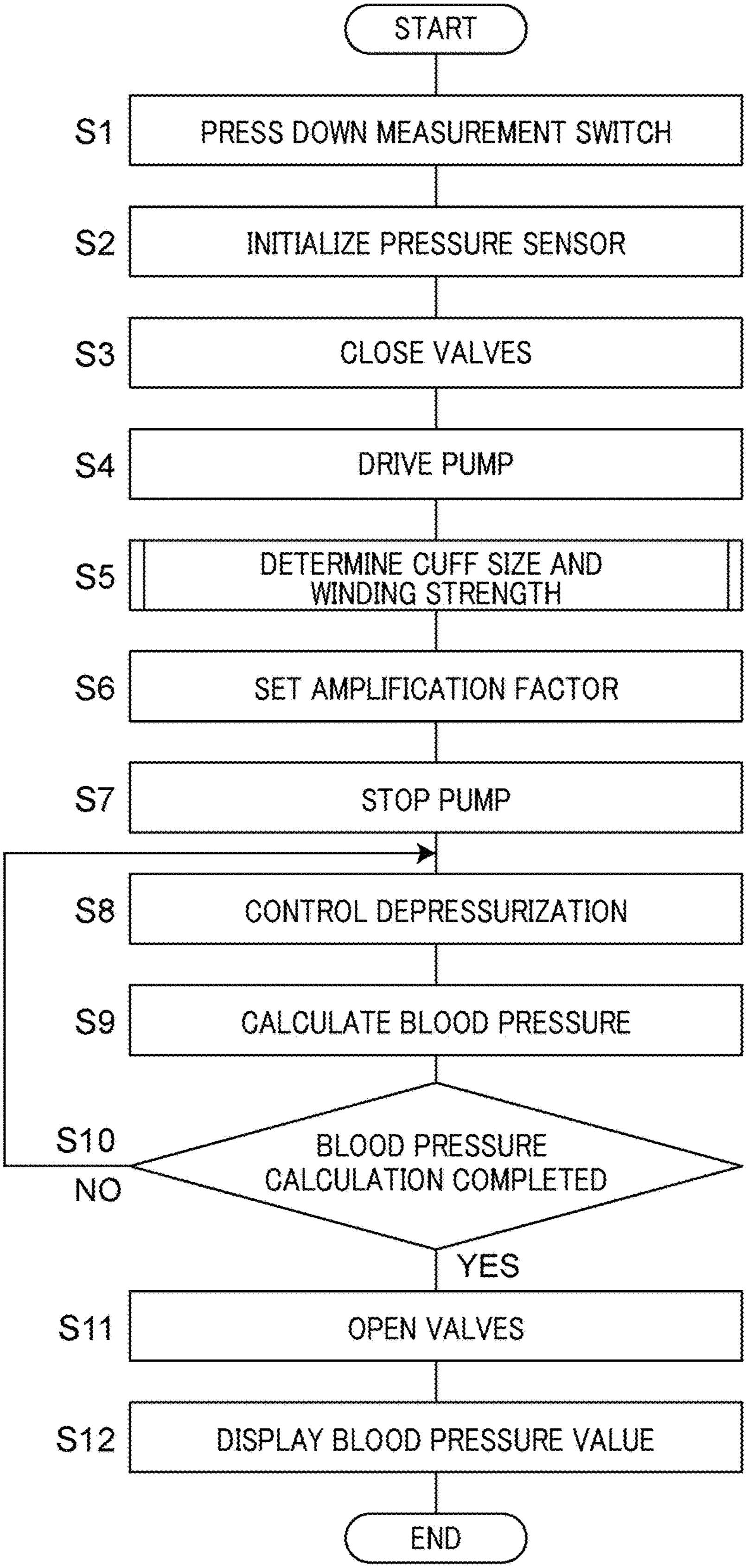
FIG. 5 is a diagram illustrating an example of a blood pressure measurement flow by the sphygmomanometer.

FIG. 5 illustrates an operation flow when a user (in this example, a subject is assumed.) performs blood pressure measurement with the sphygmomanometer 100.

When the user instructs to start the measurement using the measurement switch 52 provided on the main body 10 in the worn state where the cuff 20 is worn on the site 90 to be measured (step S1 in FIG. 5), the control unit 110 performs initialization (step S2 in FIG. 5). Specifically, the control unit 110 initializes a processing memory area and stops the pump 32, and performs 0 mmHg adjustment (The atmospheric pressure is set to 0 mmHg.) of the pressure sensor 31 in a state where the control valve 33 is opened. At this time, the atmosphere release valve 34 is in an open state.

Next, the control unit 110 closes the atmosphere release valve 34 and closes the control valve 33 (step S3). The reason why the atmosphere release valve 34 is closed at this stage after the cuff 20 is worn on the site 90 to be measured and before the pressurization of the pressing fluid bag 23 is started is to seal an appropriate amount of air in the sound acquisition fluid bag 22 in order to acquire the Korotkoff sound from the site 90 to be measured via the pressing fluid bag 23. Furthermore, closing the atmosphere release valve 34 reduces background noise, and thus contributes to improvement of a signal-to-noise ratio (S/N ratio) when acquiring the Korotkoff sound.

Subsequently, the control unit 110 acts as a pressure control unit, and drives the pump 32 to start pressurization of the cuff 20 (step S4). That is, the control unit 110 supplies air from the pump 32 to (the pressing fluid bag 23 included in) the cuff 20 through the air pipe 38. At the same time, the pressure sensor 31 acts as a pressure detection unit to detect the pressure of the pressing fluid bag 23 through the air pipe 38. The control unit 110 controls a pressurization rate by the pump 32 based on an output of the pressure sensor 31.

At this time, expansion of the pressing fluid bag 23 illustrated in FIG. 4A in a direction away from the site 90 to be measured together with the sound acquisition fluid bag 22 is regulated by the outer cloth 21 as a whole. Therefore, the pressing fluid bag 23 expands in a direction of pressing a facing region 90A of the site 90 to be measured. As a result, the region 90A of the site 90 to be measured facing the pressing fluid bag 23 is pressed, and the artery 91 passing through the region 90A is ischemic.

In this pressurization process, the control unit 110 acts as an amplification factor setting unit, and first determines a cuff size and a winding strength of the cuff 20 currently connected (step S5 in FIG. 5). Here, the control unit 110 may display the determined cuff size and winding strength on the display 50, for example, as "M cuff snug winding". Subsequently, the control unit 110 variably sets an amplification factor $\alpha$ for the amplifier circuit 350 (see FIG. 2) according to the determined cuff size and winding strength (step S6 in FIG. 5). The processing in steps S5 and S6 will be described in detail later.

Next, in this example, the control unit 110 determines whether or not the pressure (cuff pressure Pc) of the cuff 20 (in this example, the pressing fluid bag 23) has reached a predetermined value Pu (for example, illustrated in FIG. 11) based on an output of the pressure sensor 31. Here, the value Pu may be set to be, for example, 280 mmHg so as to sufficiently exceed an assumed blood pressure value of the subject, or may be set to be a blood pressure value of the subject measured last time plus 40 mmHg. In this example, as can be seen from FIG. 11, it is assumed that Pu=230 mmHg is set in advance. The control unit 110 continues pressurization until the cuff pressure Pc reaches the above-described value Pu=230 mmHg, and stops the pump 32 when the cuff pressure Pc reaches the above-described value Pu (step S7). In the example of "M cuff snug winding" illustrated in FIG. 11, the cuff pressure Pc reaches the above-described value Pu at time t1, and the pump 32 is stopped.

Figure 11:
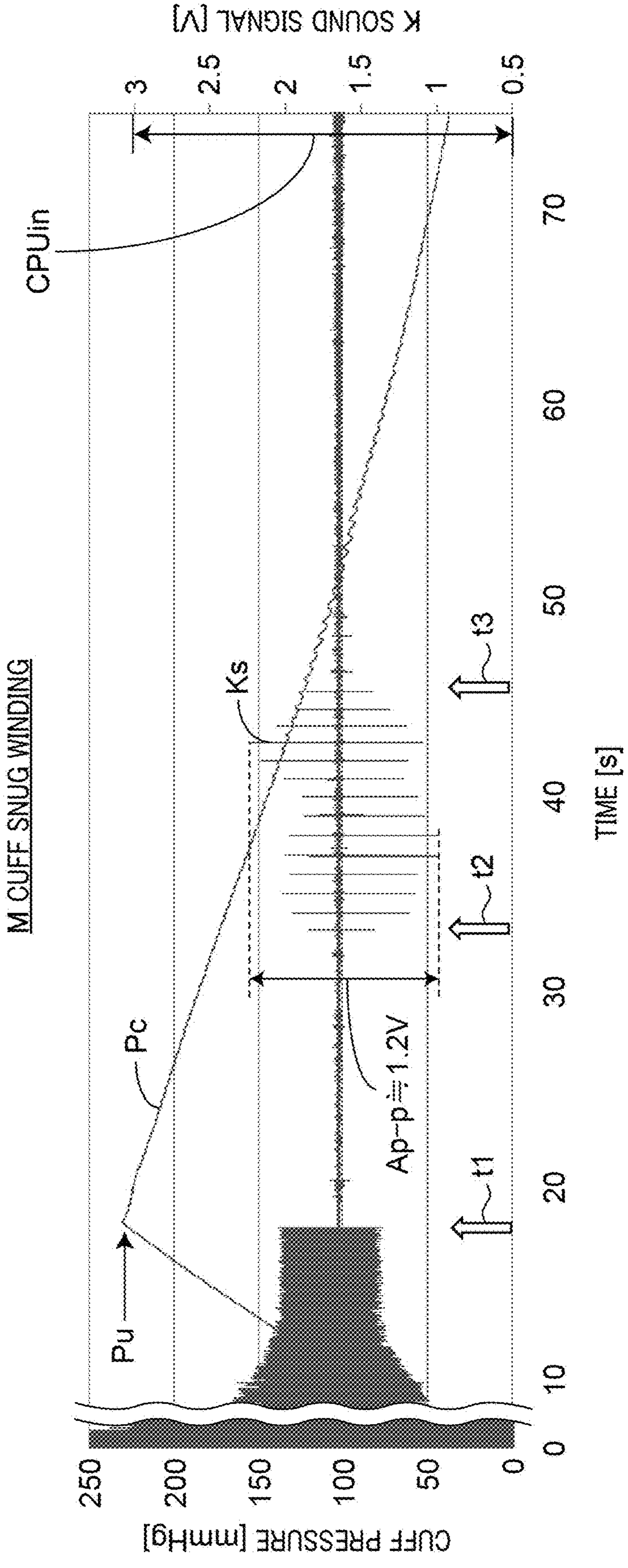
FIG. 11 is a diagram illustrating changes in a cuff pressure and a K sound signal during blood pressure measurement in a case where the cuff size of the cuff is M (medium) (This is appropriately referred to as "M cuff".) and the winding strength is the snug winding.

Subsequently, the control unit 110 gradually opens the control valve 33 (step S8 in FIG. 5). As a result, the cuff pressure Pc is reduced at a substantially constant speed. In this example, in this depressurization process, the sound acquisition fluid bag 22 acquires a sound from the site 90 to be measured via the pressing fluid bag 23. Moreover, the microphone 35 detects the sound acquired by the sound acquisition fluid bag 22 through the air pipe 37. The microphone 35 outputs an electric signal according to the sound. The filter 349 performs filtering including a fast Fourier transform (FFT) from the electrical signal output from the microphone 35 to extract a K sound signal Ks representing a Korotkoff sound. In the example of FIG. 11, the K sound signal (Korotkoff sound component) Ks starts to be observed at time t2, gradually increases to indicate a maximum value, then gradually decreases to disappear at time t3. The amplifier circuit 350 amplifies the K sound signal Ks output from the filter 349 with the amplification factor $\alpha$ variably set in step S6 described above. The amplified K sound signal $\alpha$Ks is input to the control unit 110.

The control unit 110 works as a blood pressure calculation unit together with the amplifier circuit 350, and attempts to calculate a blood pressure value (systolic blood pressure (SYS) and diastolic blood pressure (DIA)) based on the amplified K sound signal $\alpha$Ks acquired at this time (step S9 in FIG. 5). In the example of FIG. 11, the cuff pressure Pc detected by the pressure sensor 31 at time t2 is calculated as the systolic blood pressure SYS. Furthermore, the cuff pressure Pc detected by the pressure sensor 31 at time t3 is calculated as the diastolic blood pressure DIA.

Figure 4C:
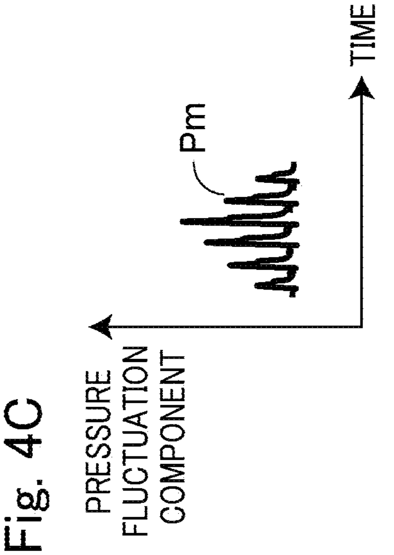
FIG. 4C is a diagram schematically illustrating a pressure fluctuation component acquired by a pressure sensor through the pressing fluid bag.

Furthermore, a pulse wave signal (pressure fluctuation component) Pm (illustrated in FIG. 4C) as pulse wave information by a pulse wave is superimposed on the cuff pressure Pc detected by the pressure sensor 31 from the pressing fluid bag 23 through the air pipe 38. In this example, the control unit 110 calculates a pulse rate PULSE (beats/min) on the basis of the pulse wave signal Pm.

In a case where the blood pressure value and the pulse rate cannot be calculated yet due to lack of data (NO in step S10 in FIG. 5), the control unit 110 repeats the processing of steps S8 to S10 until the blood pressure value and the pulse rate can be calculated.

When the blood pressure value and the pulse rate can be calculated in this manner (Yes in step S10), the control unit 110 acts as a pressure control unit, opens the control valve 33, and performs control to rapidly exhaust the air in the cuff 20 (pressing fluid bag 23) (step S11). Furthermore, the atmosphere release valve 34 is opened.

Thereafter, the control unit 110 displays the calculated blood pressure value and pulse rate on the display 50 (step S12), and performs control to store the blood pressure value and the pulse rate in the memory 51.

In this manner, in the sphygmomanometer 100 including the cuff 20, the sound acquisition fluid bag 22 acquires the sound from the site 90 to be measured via the pressing fluid bag 23.

(Change of K Sound Signal by Cuff Size and Winding Strength)

The present inventors have noted the fact that an amplitude Ap-p of the K sound signal Ks output by the filter 349 varies relatively largely depending on the cuff size and the winding strength of the currently connected cuff 20. Note that, as described above, the cuffs 20 having cuff sizes L (large), M (medium), and S (small) are referred to as "L cuff", "M cuff", and "S cuff", respectively. Furthermore, the case where the winding strength is loose, the case where the winding strength is just right, and the case where the winding strength is tight are referred to as "loose winding", "snug winding", and "tight winding", respectively.

For example, in the example of "M cuff snug winding" illustrated in FIG. 11, the amplitude of the K sound signal Ks output from the filter 349 is Ap-p≈1.2 V (volt). On the other hand, in the example of "L cuff snug winding" illustrated in FIG. 10, the amplitude of the K sound signal Ks output by the filter 349 is Ap-p≈0.3 V. Furthermore, in the example of the "S cuff snug winding" illustrated in FIG. 12, the amplitude of the K sound signal Ks output by the filter 349 is Ap-p≈1.4 V. As described above, when the cuff size (corresponding to the peripheral length of the site 90 to be measured) changes from the L cuff to the S cuff, the amplitude Ap-p of the K sound signal Ks output from the filter 349 changes from about 0.3 V to about 1.4 V (however, under the condition of "snug winding".).

Figure 13:
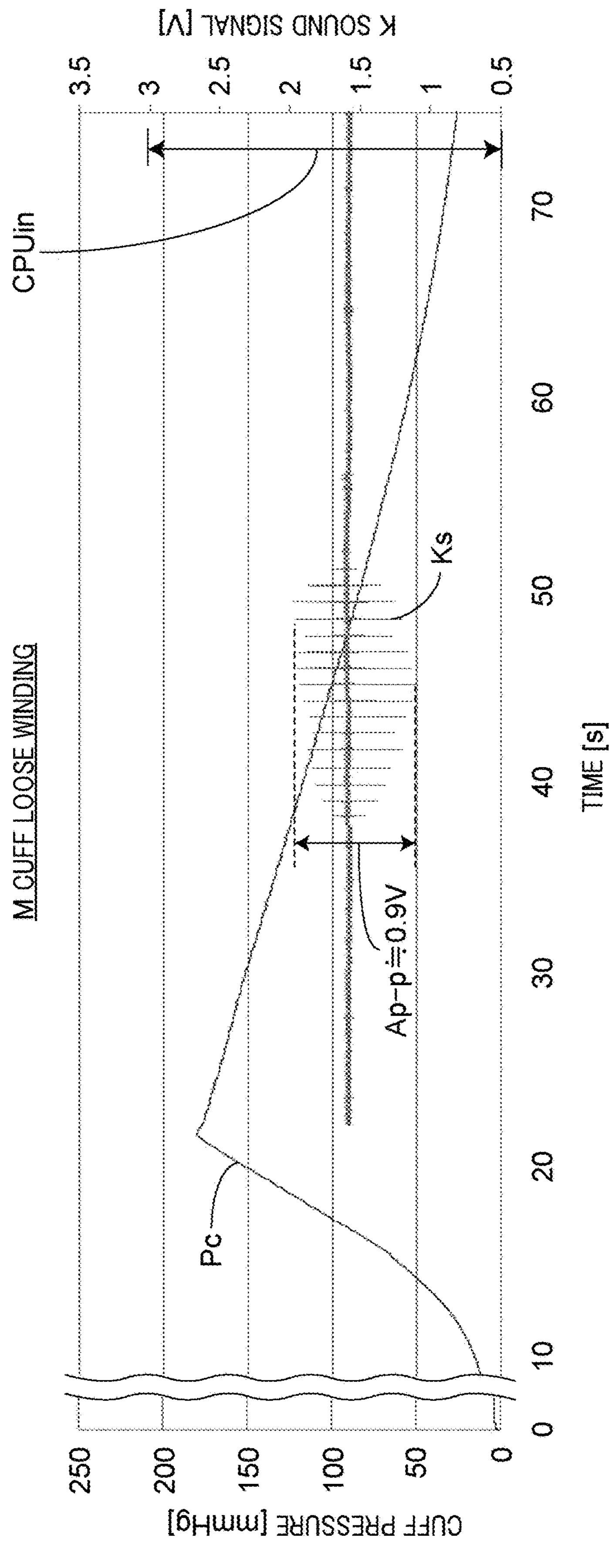
FIG. 13 is a diagram illustrating changes in a cuff pressure and a K sound signal during blood pressure measurement in a case where the cuff is an M cuff and the winding strength is loose (This is appropriately referred to as "loose winding".).
Figure 14:
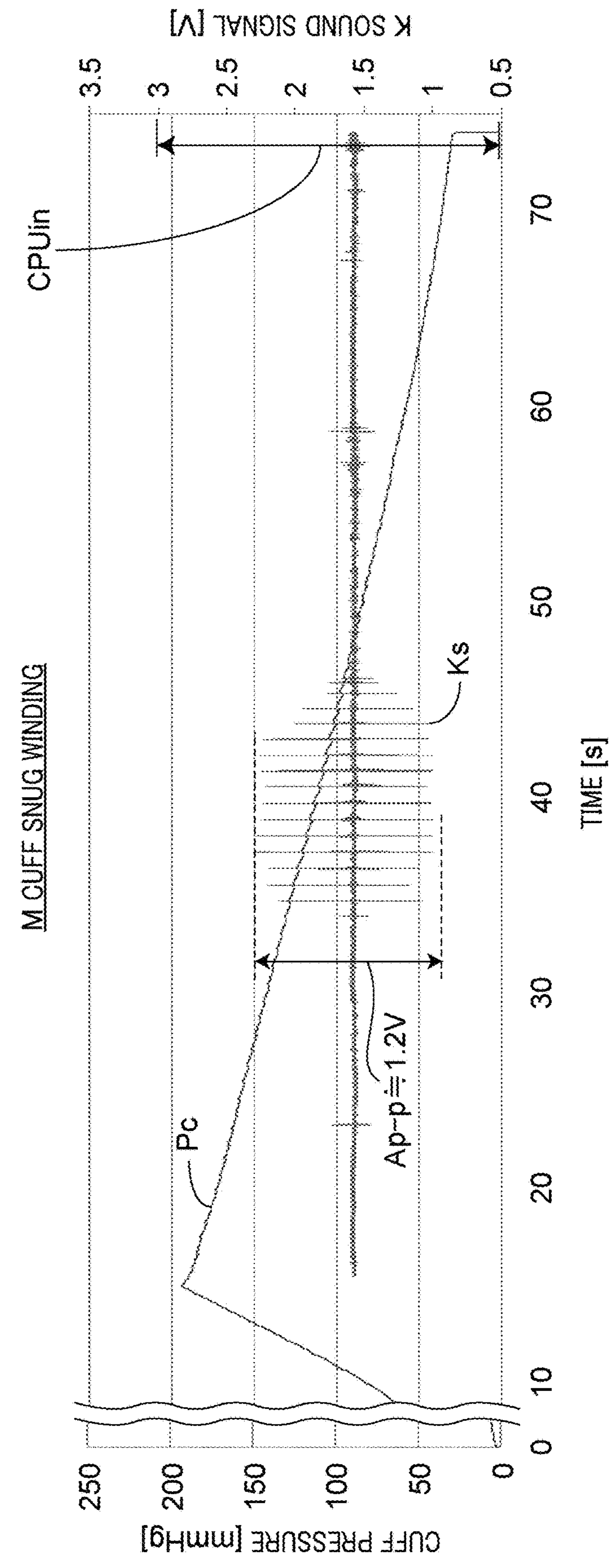
FIG. 14 is a diagram illustrating changes in a cuff pressure and a K sound signal during blood pressure measurement in a case where the cuff is an M cuff and the winding strength is the snug winding.

Furthermore, in the example of the "M cuff snug winding" illustrated in FIG. 14, the amplitude of the K sound signal Ks output by the filter 349 is Ap-p≈1.2 V, similarly to the case in FIG. 11. On the other hand, in the example of the "M cuff loose winding" illustrated in FIG. 13, the amplitude of the K sound signal Ks output by the filter 349 is Ap-p≈0.9 V. Furthermore, in the example of the "M cuff tight winding" illustrated in FIG. 15, the amplitude of the K sound signal Ks output by the filter 349 is Ap-p≈1.5 V. As described above, when the winding strength changes from "loose winding" to "tight winding", the amplitude Ap-p of the K sound signal Ks output from the filter 349 changes from about 0.9 V to about 1.5 V (however, under the condition of "M cuff".).

Here, as illustrated in FIGS. 10 to 15, an input range CPUin of the CPU included in the control unit 110 is 2.5 V (constant range) from 0.5 V to 3.0 V. For this reason, for example, if the amplification factor $\alpha$ is set to be large on the basis of the Korotkoff sound level (the amplitude Ap-p of the K sound signal Ks) in the case of "L cuff loose winding", there arises a problem that the K sound signal $\alpha$Ks amplified with the amplification factor $\alpha$ is saturated (exceeds the input range CPUin) in the case of "S cuff tight winding".

Therefore, the present inventors have conceived the invention of determining the cuff size and the winding strength of the currently connected cuff 20 (step S5 in FIG. 5), and variably setting the amplification factor $\alpha$ for the amplifier circuit 350 (see FIG. 2) according to the determined cuff size and winding strength (step S6 in FIG. 5).

(Determination of Cuff Size and Winding Strength)

Figure 8:
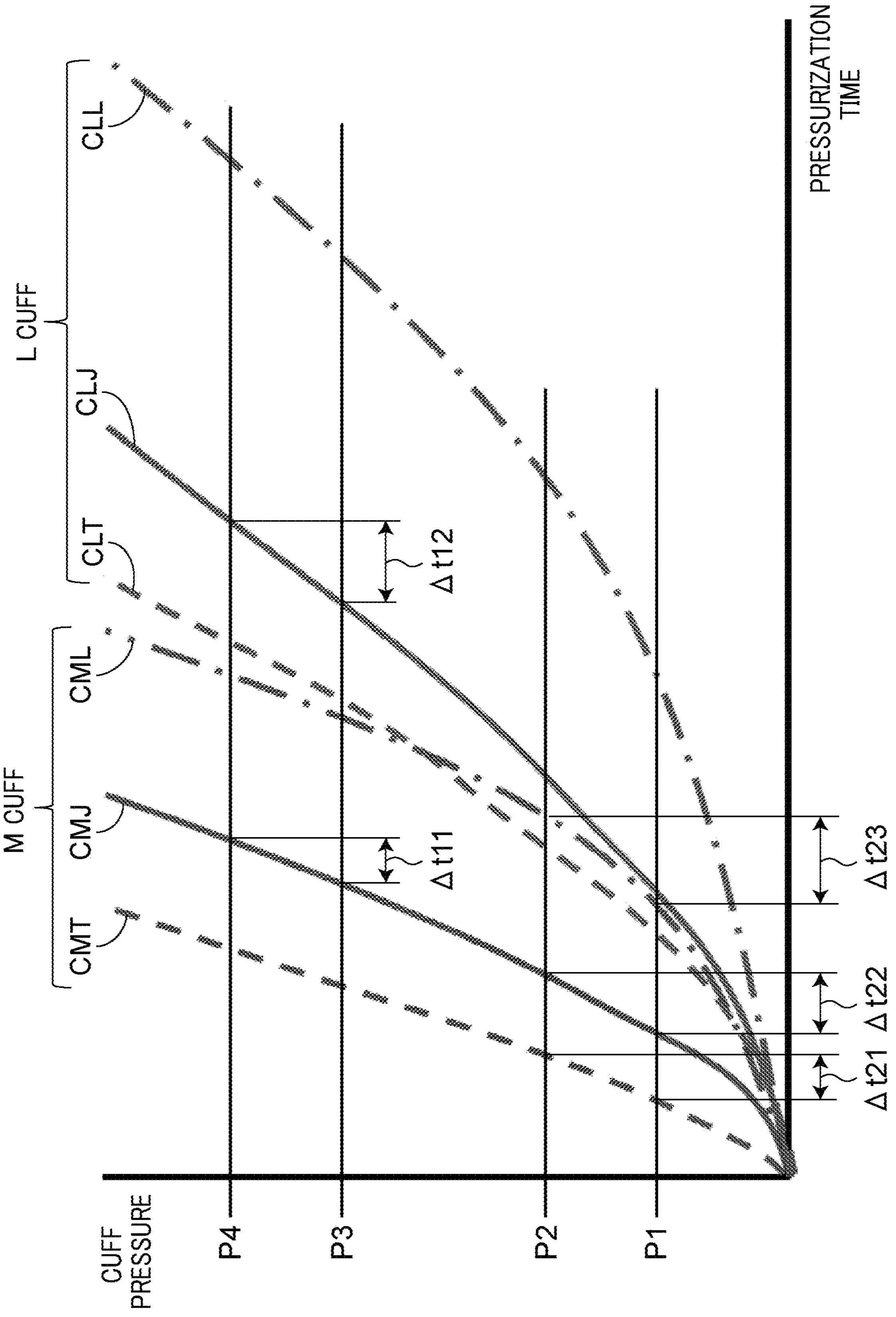
FIG. 8 is a diagram illustrating a relationship between a pressure (cuff pressure) of the pressing fluid bag included in the cuff and pressurization time in a case where the cuff size and the winding strength of the cuff are changed.

FIG. 8 illustrates a relationship between the pressure (cuff pressure Pc) of the pressing fluid bag 23 included in the cuff 20 and the pressurization time in a case where the cuff size and the winding strength of the cuff 20 are changed. In the example of FIG. 8, curves CLL, CLJ, and CLT representing the increase in the cuff pressure Pc with the elapse of the pressurization time in the case of "L cuff loose winding", "L cuff snug winding", and "L cuff tight winding", respectively, are represented. Furthermore, curves CML, CMJ, and CMT representing the increase in the cuff pressure Pc with the elapse of the pressurization time in the case of "M cuff loose winding", "M cuff snug winding", and "M cuff tight winding", respectively, are represented.

For example, as disclosed in Patent Literature 3 (JP 5408142 B2), in a predetermined first pressure range of 20 mmHg or more (This is a range of P3 to P4 illustrated in FIG. 8, which in this example is a range of 25 mmHg to 35 mmHg. This is called a "first pressure range (P3, P4)".), a first passage time Δt1 required for the cuff pressure Pc to pass through the first pressure range (P3, P4) changes according to the peripheral length (corresponding to the cuff size, in particular, the size of the pressing fluid bag 23) of the site to be measured regardless of the winding strength of the cuff 20. For example, in the example in FIG. 8, it can be seen that a first passage time Δt12 for the curve CLJ of "L-cuff snug winding" is greater than a first passage time Δt11 for the curve CMJ of "M-cuff snug winding". Therefore, the cuff size can be determined according to the first passage time Δt1 for the currently connected cuff 20.

Furthermore, for example, as disclosed in Patent Literature 3 (JP 5408142 B2), in a predetermined second pressure range below the first pressure range (P3, P4) (This is a range of P1 to P2 illustrated in FIG. 8, which in this example is a range of 10 mmHg to 15 mmHg. This is called a "second pressure range (P1, P2)".), a second passage time Δt2 required for the cuff pressure Pc to pass through the second pressure range (P1, P2) changes according to the cuff size and the winding strength. That is, under the condition set to a certain cuff size, the second passage time Δt2 corresponds to the winding strength of the cuff 20. For example, in the example in FIG. 8, it can be seen that a second passage time Δt22 for the curve CMJ of "M cuff snug winding" is larger than a second passage time Δt21 for the curve CMT of "M cuff tight winding", and further, a second passage time Δt23 for the curve CML of "M cuff loose winding" is larger. The same applies to the L cuff. Therefore, for the currently connected cuff 20, the winding strength can be determined according to the cuff size and the second passage time Δt2.

Figure 6:
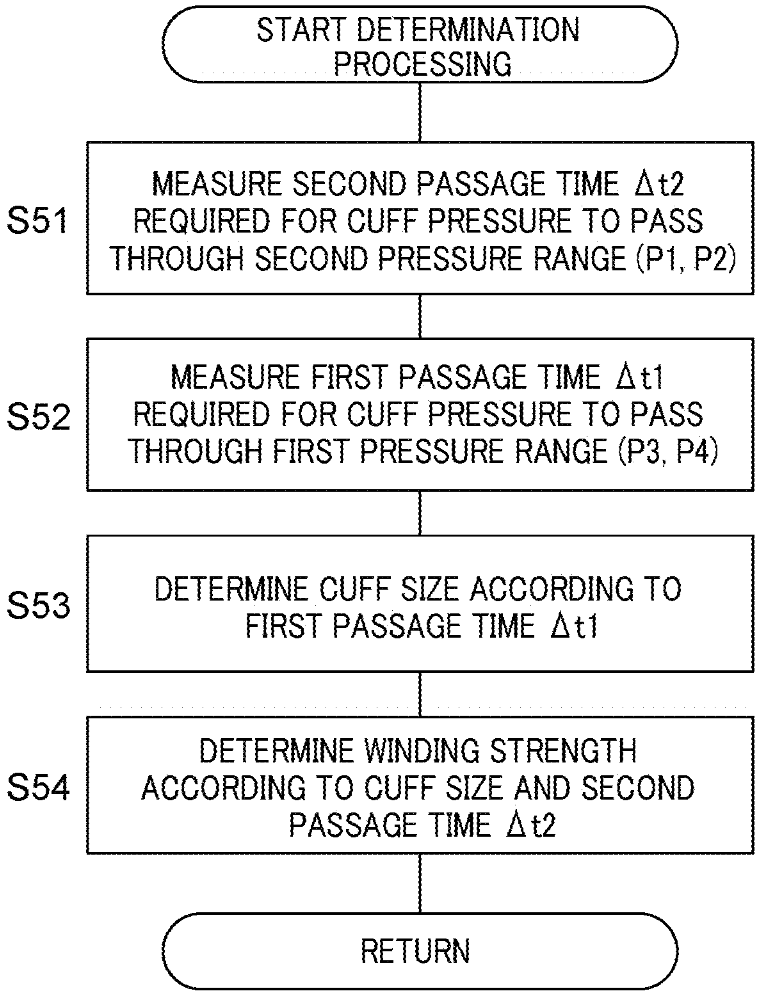
FIG. 6 is a diagram illustrating a flow of determination processing of determining a cuff size and a winding strength of the cuff in the blood pressure measurement flow of FIG. 5.

FIG. 6 illustrates a specific flow of step S5 in FIG. 5 based on the above-described knowledge. First, the control unit 110 measures the second passage time Δt2 required for the cuff pressure Pc to pass through the second pressure range (P1, P2) in the pressurization process as shown in step S51 of FIG. 6. Subsequently, in the pressurization process, as shown in step S52, the control unit 110 measures the first passage time Δt1 required for the cuff pressure Pc to pass through the first pressure range (P3, P4).

Next, the control unit 110 determines the cuff size of the cuff 20 currently connected according to the first passage time Δt1 measured in step S52 (step S53). Specifically, as illustrated along a horizontal axis (representing the first passage time Δt1) in FIG. 9, a range Δt1S from a lower limit value to an upper limit value to be taken by the first passage time Δt1 corresponding to the S cuff, a range Δt1M from a lower limit value to an upper limit value to be taken by the first passage time Δt1 corresponding to the M cuff, and a range Δt1L from a lower limit value to an upper limit value to be taken by the first passage time Δt1 corresponding to the L cuff are determined in advance on the basis of actual measurement. Then, the cuff size of the currently connected cuff 20 is determined according to which range Δt1S, Δt1M, or Δt1L the measured first passage time Δt1 falls within.

Next, the control unit 110 determines the winding strength of the currently connected cuff 20 according to the cuff size determined in step S53 of FIG. 6 and the second passage time Δt2 measured in step S51 (step S54). Specifically, for each cuff size, ranges to be taken by the second passage times Δt2 corresponding to "loose winding", "snug winding", and "tight winding" are determined in advance on the basis of actual measurement. Then, for each cuff size, the winding strength of the currently connected cuff 20 is determined according to which range the measured second passage time Δt2 falls within.

(Setting of Amplification Factor)

Figure 9:
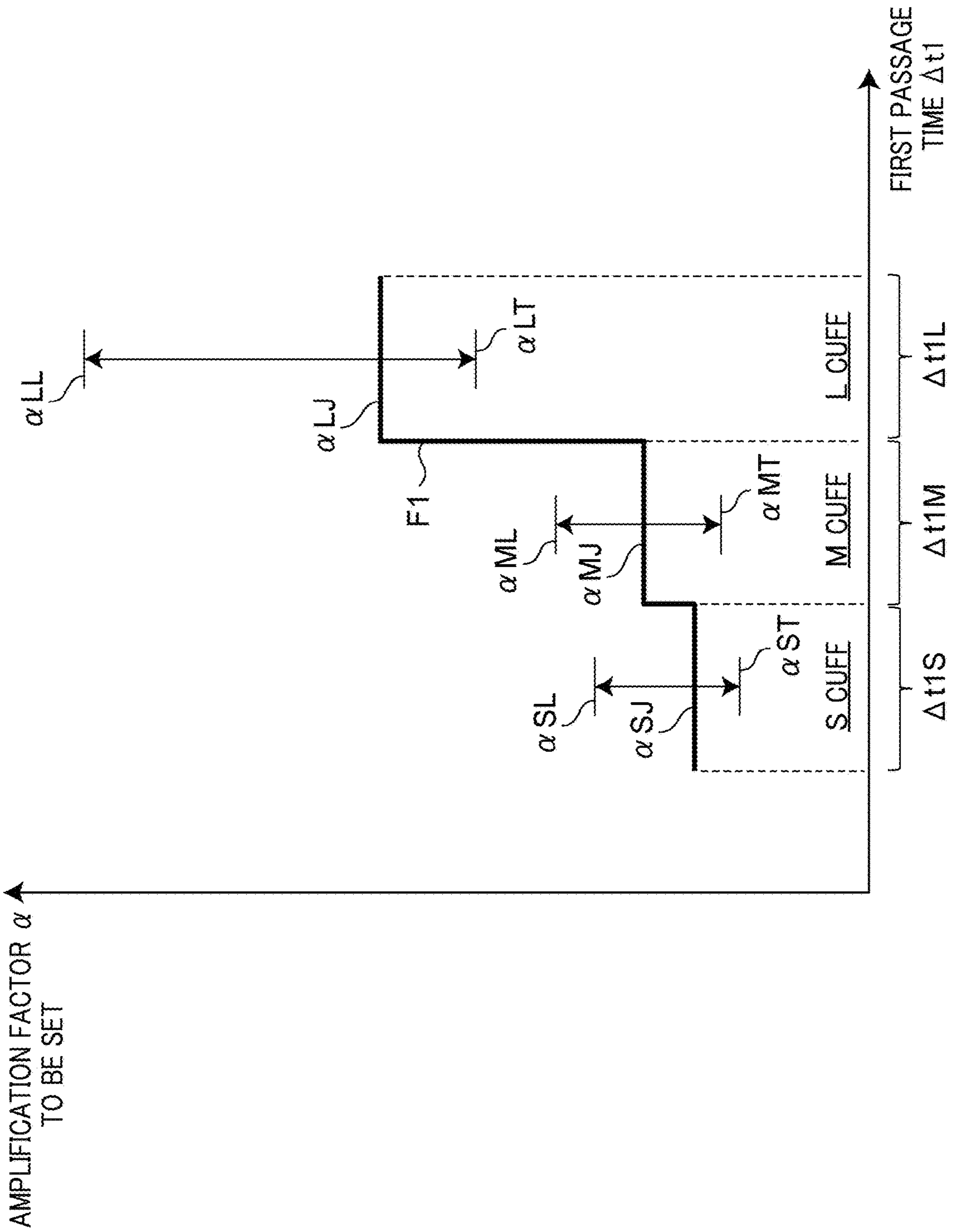
FIG. 9 is a diagram for explaining how to variably set an amplification factor for a Korotkoff sound component according to the cuff size and winding strength of the cuff.

FIG. 9 illustrates how the control unit 110 acts as an amplification factor setting unit to variably set the amplification factor α for the K sound signal (Korotkoff sound component) Ks according to the cuff size and the winding strength of the cuff 20 currently connected in step S6 of FIG. 5. In this example, basically, the amplification factor α is variably set so as to reduce or eliminate the change of the Korotkoff sound level (the amplitude Ap-p of the K sound signal Ks). Specifically, amplification factors αLJ, αMJ, and αSJ for "snug winding" are determined as a function F1 that changes stepwise according to which of the L cuff, the M cuff, and the S cuff the cuff size is, that is, which of the ranges Δt1S, Δt1M, and Δt1L the first passage time Δt1 enters. Amplification factors for "loose winding" and "tight winding" are determined as variations for each cuff size. In the example of FIG. 9, for the L cuff, an amplification factor for "loose winding" is defined as αLL (>αLJ), and an amplification factor for "tight winding" is defined as αLT (<αLJ). For the M cuff, an amplification factor for "loose winding" is defined as αML (>αMJ), and an amplification factor for "tight winding" is defined as αMT (<αMJ). Furthermore, for the S cuff, an amplification factor for "loose winding" is defined as αSL (>αSJ), and an amplification factor for "tight winding" is defined as αST (<αSJ). The value of the amplification factor α variably set in this manner is, for example, as shown in Table 2 below.

TABLE 2

| | Amplification factor α [times] | | |
|---|---|---|---|
| | Loose winding | Snug winding | Tight winding |
| L cuff | αLL = 12.5 | αLJ = 8.3 | αLT = 7.4 |
| M cuff | αML = 2.9 | αMJ = 2.1 | αMT = 1.7 |
| S cuff | αSL = 2.7 | αSJ = 1.8 | αST = 1.6 |

As described above, the amplifier circuit 350 amplifies the K sound signal Ks with the amplification factor α variably set in this manner. As a result, it is possible to reduce or eliminate the change of the Korotkoff sound level (the amplitude Ap-p of the K sound signal Ks) depending on the cuff size and the winding strength. The amplified K sound signal αKs is input to the control unit 110. Therefore, the amplified K sound signal αKs does not exceed the input range CPUin of the CPU included in the control unit 110. Therefore, according to the sphygmomanometer 100, the blood pressure can be accurately measured.

(Modification 1)

In the above example, the control unit 110 calculates the blood pressure value in the depressurization process, but the present invention is not limited thereto, and the blood pressure value may be calculated in the pressurization process of the cuff 20 (the pressing fluid bag 23 included in the cuff). For example, FIG. 7 illustrates a blood pressure measurement flow in a case where the blood pressure value is calculated in a part after exceeding the first pressure range (P3, P4) in the pressurization process.

Figure 7:
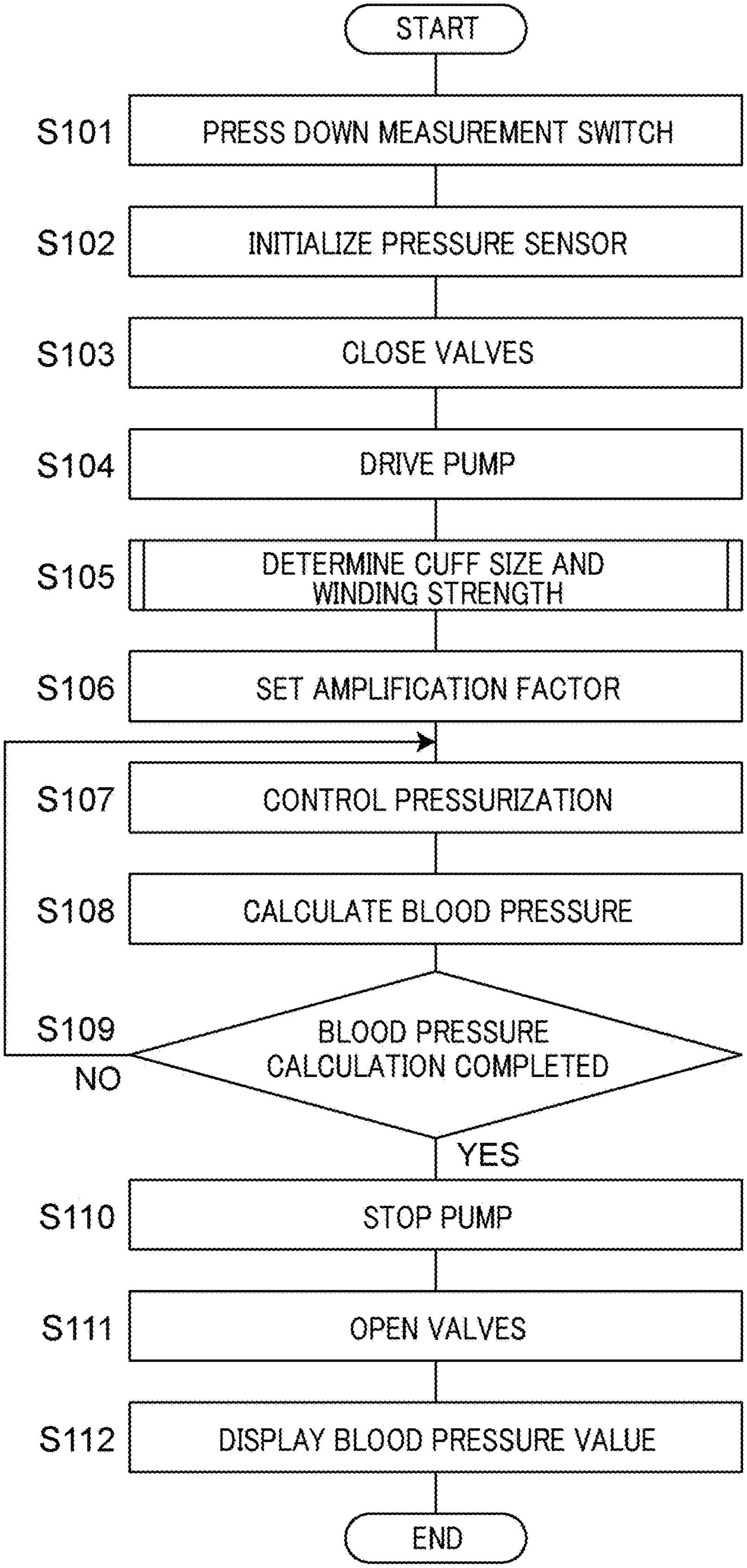
FIG. 7 is a diagram illustrating another example of a blood pressure measurement flow by the sphygmomanometer.

In the blood pressure measurement flow of FIG. 7, the control unit 110 advances the processing from the pressing down of the measurement switch (step S101) to the setting of the amplification factor (step S106) in exactly the same manner as steps S1 to S6 of FIG. 5. Subsequently, in step S107 of FIG. 7, the control unit 110 acts as a pressure control unit to continue the pressurization control, and attempts to calculate a blood pressure value and a pulse rate in the pressurization process (that is, the part after exceeding the first pressure range (P3, P4)) (step S108). When the blood pressure value and the pulse rate can be calculated (Yes in step S109), the control unit 110 acts as a pressure control unit, stops the pump (step S110), opens the control valve 33, and performs control to rapidly exhaust the air in the cuff 20 (pressing fluid bag 23) (step S111). Furthermore, the atmosphere release valve 34 is opened. Thereafter, the control unit 110 displays the calculated blood pressure value and pulse rate on the display 50 (step S112), and performs control to store the blood pressure value and the pulse rate in the memory 51.

Also in the blood pressure measurement flow of FIG. 7, the blood pressure can be accurately measured as in the blood pressure measurement flow of FIG. 5.

(Modification 2)

Figure 10:
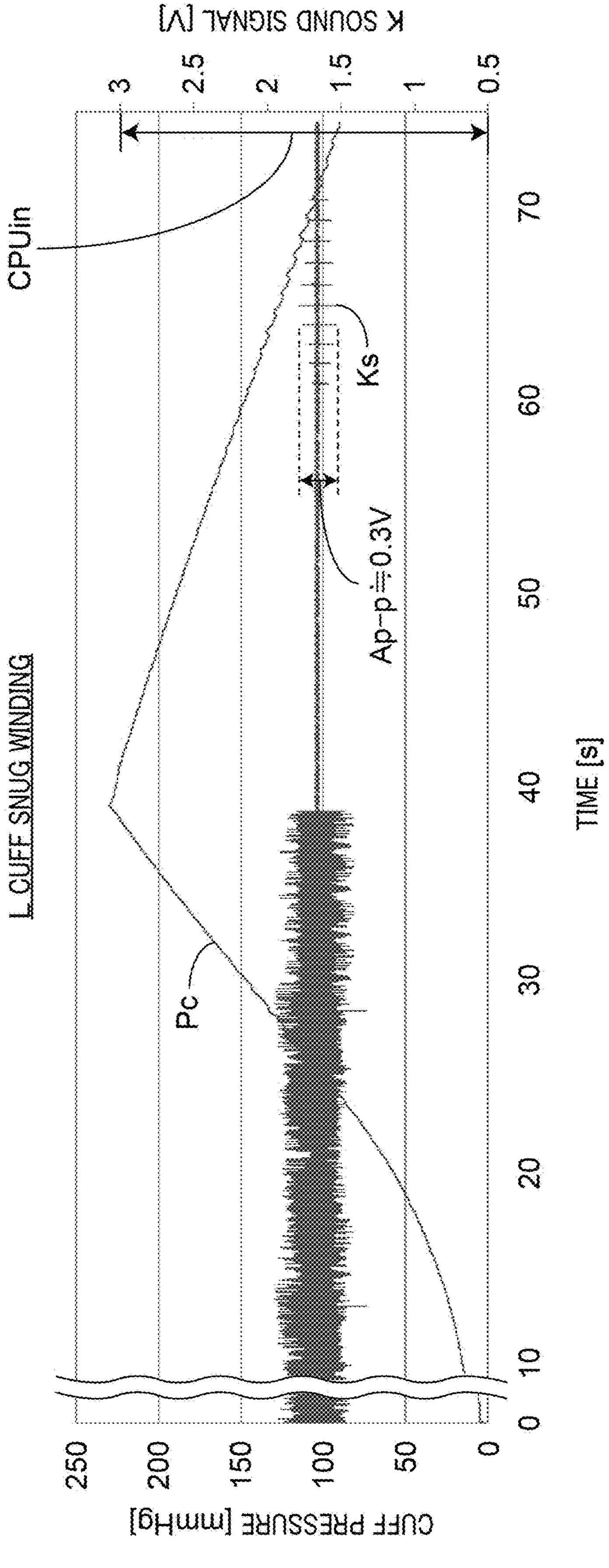
FIG. 10 is a diagram illustrating changes in a cuff pressure and a K sound signal during blood pressure measurement in a case where the cuff size of the cuff is L (large) (This is appropriately referred to as "L cuff".) and the winding strength is just right (This is appropriately referred to as "snug winding".).
Figure 12:
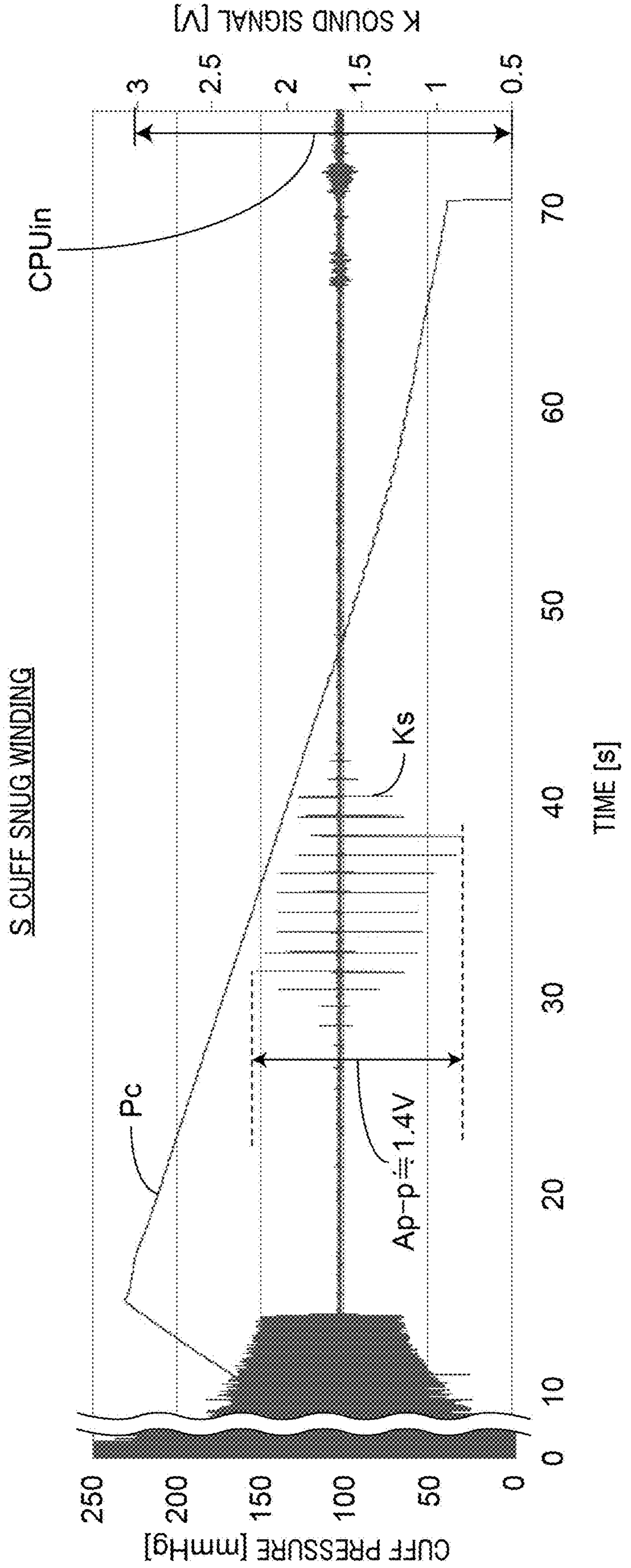
FIG. 12 is a diagram illustrating changes in a cuff pressure and a K sound signal during blood pressure measurement in a case where the cuff size of the cuff is S (small) (This is appropriately referred to as "S cuff".) and the winding strength is the snug winding.
Figure 15:
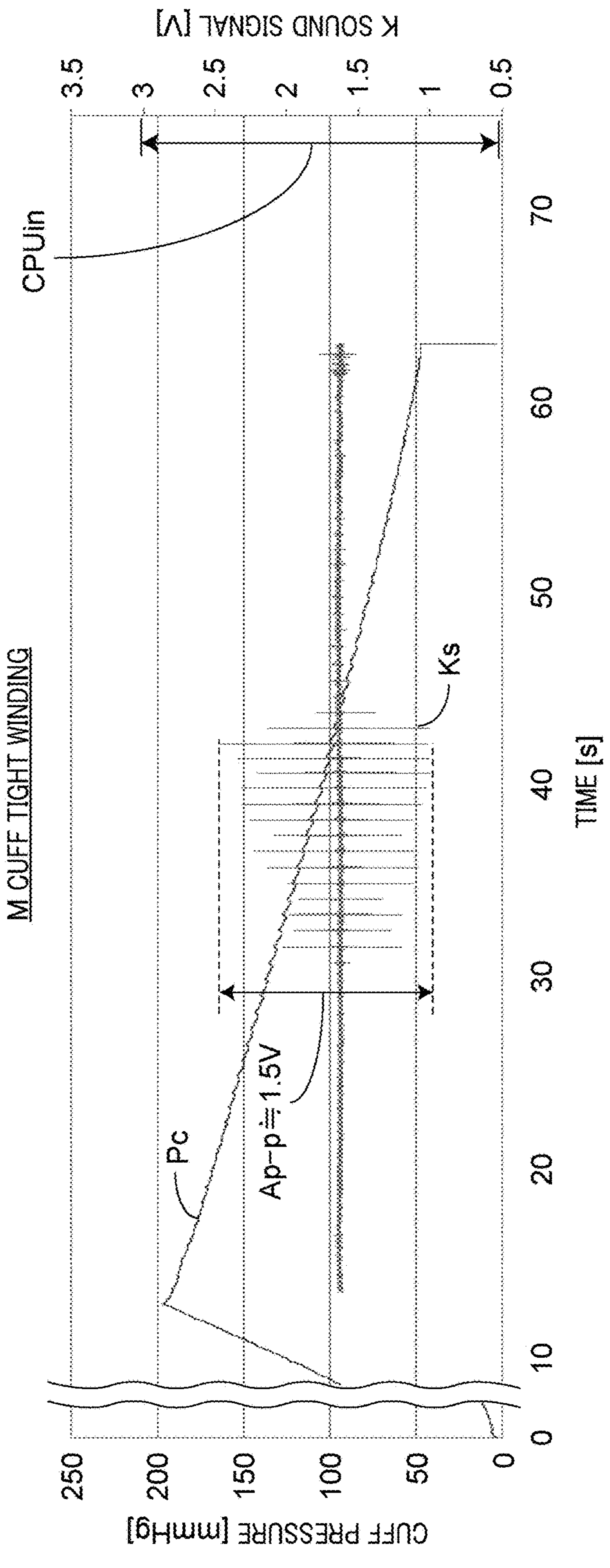
FIG. 15 is a diagram illustrating changes in a cuff pressure and a K sound signal during blood pressure measurement in a case where the cuff is an M cuff and the winding strength is tight (This is appropriately referred to as "tight winding".).

As illustrated in FIGS. 10 to 12, when the cuff size changes from the L cuff to the S cuff, the amplitude Ap-p of the K sound signal Ks output from the filter 349 changes from about 0.3 V to about 1.4 V (however, under the condition of "snug winding".). Furthermore, as illustrated in FIGS. 13 to 15, when the winding strength changes from "loose winding" to "tight winding", the amplitude Ap-p of the K sound signal Ks output from the filter 349 changes from about 0.9 V to about 1.5 V (however, under the condition "M cuff".). Thus, the influence of the change in cuff size on the amplitude Ap-p of the K sound signal Ks is greater than the winding strength. Therefore, instead of variably setting the amplification factor α for the K sound signal Ks according to both the cuff size and the winding strength of the currently connected cuff 20, the amplification factor α for the K sound signal Ks may be variably set only according to the cuff size.

In this case, the control unit 110 acts as an amplification factor setting unit, and may variably set the amplification factor α as αLJ, αMJ, and αSJ depending on whether the cuff size of the currently connected cuff 20 is the L cuff, the M cuff, or the S cuff, that is, whether the first passage time Δt1 falls within any of the ranges Δt1S, Δt1M, and Δt1L, for example, as indicated by the function F1 changing stepwise in FIG. 9. In this case, it is possible to reduce or eliminate the change of the amplitude Ap-p (Korotkoff sound level) of the K sound signal Ks depending on the cuff size. As a result, the amplified K sound signal αKs does not exceed the input range CPUin of the CPU included in the control unit 110.

Therefore, the blood pressure can be accurately measured. At the same time, the determination processing (FIG. 6) can be simplified.

(Modification 3)

In the above example, the first passage time Δt1 is measured (step S52), and the cuff size is determined according to the first passage time Δt1 (step S53). However, the present invention is not limited thereto. For example, the measurement switch 52 may be used as an input unit to input size information indicating which cuff size (for example, an L cuff, an M cuff, or an S cuff) the currently connected cuff 20 has among a plurality of types of cuff sizes prepared in advance.

The size information can be input as follows, for example. First, when the user presses the measurement switch 52 for three seconds or longer, the control unit 110 enters a size information input mode. In this size information input mode, the control unit 110 inputs size information indicating the L cuff, the M cuff, or the S cuff according to the number of times the measurement switch 52 is pressed.

In a case where the size information is input, the control unit 110 acts as an amplification factor setting unit to variably set an amplification factor with respect to the amplification factor α for the K sound signal Ks according to the input size information instead of obtaining the first passage time Δt1.

Also in this case, it is possible to reduce or eliminate the change of the amplitude Ap-p (Korotkoff sound level) of the K sound signal Ks depending on the cuff size. Therefore, the blood pressure can be accurately measured. At the same time, the determination processing (FIG. 6) can be simplified.

(Modification 4)

In the above example, as illustrated in FIG. 9, the amplification factors αLJ, αMJ, and αSJ for "snug winding" are determined as the function F1 changing stepwise according to which range Δt1S, Δt1M, and Δt1L the first passage time Δt1 enters. However, the present invention is not limited thereto. For example, the amplification factor α may be variably set according to a curve that monotonically increases as the first passage time Δt1 increases.

In the above example, L (large), M (medium), and S (small) are set as the cuff size for the upper arm, but the cuff size is not limited thereto. An extra large (XL) size larger than the L size can also be set for the upper arm. Furthermore, a wrist size smaller than the upper arm S size can also be set. In this case, in the sphygmomanometer 100, the amplification factor α with respect to the K sound signal Ks is variably set according to the cuff size.

In the above example, the microphone 35 as a sound detection device is mounted on the main body 10 and detects the sound from the sound acquisition fluid bag 22 through the air pipe 37, but the present invention is not limited thereto. The microphone 35 as the sound detection device may be mounted on the cuff 20 in a state of being in contact with the sound acquisition fluid bag 22, and may directly detect the sound from the sound acquisition fluid bag 22.

The site 90 to be measured is not limited to the upper arm, and may be an upper limb other than the upper arm such as a wrist or a lower limb such as an ankle.

As described above, a sphygmomanometer that measures a blood pressure by a Korotkoff sound generated by a site to be measured, the sphygmomanometer of the present disclosure comprises:

a blood pressure measuring cuff worn around the site to be measured;

a pressure device that supplies a fluid to the blood pressure measuring cuff to pressurize the blood pressure measuring cuff, or discharges a fluid from the blood pressure measuring cuff to depressurize the blood pressure measuring cuff;

a sound detection device that detects a sound generated by the site to be measured via the blood pressure measuring cuff;

an amplification factor setting unit that measures a first passage time required for pressure of the blood pressure measuring cuff to pass through a predetermined first pressure range in a pressurization process of the blood pressure measuring cuff by the pressure device, and variably sets an amplification factor for a Korotkoff sound component according to the first passage time; and a blood pressure calculation unit that receives an output of the sound detection device according to the sound from the blood pressure measuring cuff, amplifies a Korotkoff sound component included in the output with an amplification factor set by the amplification factor setting unit, and calculates a blood pressure of the site to be measured based on the amplified Korotkoff sound component in the pressurization process or a depressurization process subsequent to the pressurization process.

In the present specification, the "site to be measured" includes an upper limb such as an upper arm and a wrist or a lower limb such as an ankle, and typically refers to a rod-like site.

The "blood pressure measuring cuff" typically includes a fluid bag (This is referred to as "pressing fluid bag".) for compressing the site to be measured.

The "pressure device" typically includes a pump and a valve.

The "sound detection device" typically includes a microphone.

The "predetermined first pressure range" refers to, for example, a range of 25 mmHg to 35 mmHg.

In the sphygmomanometer of the present disclosure, the blood pressure measuring cuff is worn to surround the site to be measured in a circumferential direction. In this worn state, for example, air is supplied to the blood pressure measuring cuff (typically, the pressing fluid bag) by the pressure device at the time of blood pressure measurement. As a result, the blood pressure measuring cuff is pressurized. As a result, the site to be measured is compressed, and the artery passing through the site to be measured is ischemic. In the pressurization process, the amplification factor setting unit measures a first passage time required for the pressure (cuff pressure) of the blood pressure measuring cuff to pass through a predetermined first pressure range.

Here, for example, as disclosed in Patent Literature 3 (JP 5408142 B2), in a predetermined first pressure range (for example, a range of 25 mmHg to 35 mmHg) of 20 mmHg or more, the first passage time required for the cuff pressure to pass through the first pressure range changes according to a peripheral length (corresponding to a cuff size, in particular, a size of a pressing fluid bag) of the site to be measured regardless of a winding strength of the cuff.

Therefore, the amplification factor setting unit variably sets the amplification factor for the Korotkoff sound component according to the first passage time. The blood pressure calculation unit receives the output of the sound detection device according to the sound from the blood pressure measuring cuff, amplifies the Korotkoff sound component included in the output with the amplification factor set by the amplification factor setting unit, and calculates the blood pressure of the site to be measured based on the amplified Korotkoff sound component in the pressurization process or the depressurization process subsequent to the pressurization process. As a result, it is possible to reduce or eliminate the change of the Korotkoff sound level depending on the peripheral length of the site to be measured. That is, it is possible to avoid a situation in which the amplified Korotkoff sound component exceeds the input range of the processor (constituting the blood pressure calculation unit) that processes this signal. Therefore, according to this sphygmomanometer, the blood pressure can be accurately measured.

In the sphygmomanometer of one embodiment, the blood pressure measuring cuff includes:

an outer cloth extending in a longitudinal direction in a band shape and surrounding the site to be measured, a pressing fluid bag that is provided to extend along the longitudinal direction on a side of the outer cloth facing the site to be measured, and compresses the site to be measured;

a sound acquisition fluid bag that is provided between the outer cloth and the pressing fluid bag in a thickness direction perpendicular to the outer cloth, and acquires a sound from the site to be measured via the pressing fluid bag, the sphygmomanometer further comprising:

a first fluid pipe that connects the pressing fluid bag and the pressure device so as to be capable of flowing a fluid; and a second fluid pipe that connects the sound acquisition fluid bag and the sound detection device so as to be capable of flowing a fluid, separately from the first fluid pipe.

The "side facing the site to be measured" means a side facing the site to be measured in a state where the blood pressure measuring cuff is worn around the site to be measured (This is referred to as a "worn state".).

In the blood pressure measuring cuff, the "longitudinal direction" means a direction in which the outer cloth extends in a band shape, and corresponds to a circumferential direction surrounding the site to be measured in the worn state. A "width direction" described later means a direction perpendicular to the longitudinal direction in a plane along the outer cloth, and corresponds to a direction in which an artery passes through the site to be measured in the worn state. Furthermore, the "thickness direction" means a direction perpendicular to both the longitudinal direction and the width direction (that is, the outer cloth), and corresponds to a direction perpendicular to an outer peripheral surface of the site to be measured in the worn state.

In the sphygmomanometer according to this embodiment, the blood pressure measuring cuff is worn such that the longitudinal direction of the cuff surrounds the site to be measured. In this worn state, the pressing fluid bag, the sound acquisition fluid bag, and the outer cloth are arranged in this order with respect to the site to be measured in the thickness direction. In this worn state, at the time of blood pressure measurement, air is supplied from the pressure device to the pressing fluid bag through the first fluid pipe. As a result, the pressing fluid bag is pressurized. In this pressurization process, the expansion of the pressing fluid bag together with the sound acquisition fluid bag in a direction away from the site to be measured is regulated by the outer cloth as a whole. Therefore, the pressing fluid bag expands in a direction of pressing the site to be measured. As a result, the site to be measured is compressed, and the artery passing through the site to be measured is ischemic. Subsequently, air is gradually discharged from the pressing fluid bag through the first fluid pipe by the pressure device. As a result, the pressure of the pressing fluid bag is gradually reduced.

In this sphygmomanometer, in the blood pressure measuring cuff, the sound acquisition fluid bag acquires a sound from the site to be measured via the pressing fluid bag. In the worn state, the pressing fluid bag extends along the circumferential direction of the site to be measured. Therefore, even if a position (in particular, a circumferential position) where the cuff is worn with respect to the site to be measured varies, the influence on a level of the sound entering the pressing fluid bag from the artery passing through the site to be measured is small, and as a result, the sound collection by the sound acquisition fluid bag is stabilized. Therefore, the Korotkoff sound can be stably acquired. Moreover, the second fluid pipe that connects the sound acquisition fluid bag and the sound detection device so as to be capable of flowing a fluid is provided separately from the first fluid pipe that connects the pressing fluid bag and the pressure device so as to be capable of flowing a fluid. Therefore, it is possible to prevent the pulse sound (pulse wave sound) from being mixed from a fluid system (This is referred to as "first fluid system".) including the pressing fluid bag, the first fluid pipe, and the pressure device into a fluid system (This is referred to as "second fluid system".) including the sound acquisition fluid bag, the second fluid pipe, and the sound detection device. Therefore, the Korotkoff sound can be more stably acquired.

In the sphygmomanometer of one embodiment, lengths in a longitudinal direction of the blood pressure measuring cuff and/or a pressing fluid bag included in the blood pressure measuring cuff are variably set according to a peripheral length of the site to be measured, and the amplification factor setting unit sets the amplification factor to be large as the first passage time becomes longer as lengths in the longitudinal direction and/or a width direction of the blood pressure measuring cuff and/or the pressing fluid bag become longer.

In a case where the site to be measured is a thick arm (with a large peripheral length), there are many biological tissues between the artery and the body surface, so that the sound is difficult to be transmitted, and the Korotkoff sound level decreases. On the other hand, in a case where the site to be measured is a thin arm (with a small peripheral length), there is a tendency that the Korotkoff sound level increases because there are few biological tissues between the artery and the body surface. Therefore, in the sphygmomanometer according to this embodiment, the amplification factor setting unit sets the amplification factor to be large as the first passage time becomes longer as the lengths in the longitudinal direction and/or the width direction of the blood pressure measuring cuff and/or the pressing fluid bag become longer. Therefore, it is possible to reliably reduce or eliminate the change of the Korotkoff sound level depending on the peripheral length of the site to be measured. As a result, the blood pressure calculation unit can measure the blood pressure with higher accuracy.

In the sphygmomanometer of one embodiment, the amplification factor setting unit measures a second passage time required for the pressure of the blood pressure measuring cuff to pass through a predetermined second pressure range below the first pressure range in the pressurization process of the blood pressure measuring cuff by the pressure device, and sets the amplification factor to be large as the second passage time becomes longer as a winding strength of the blood pressure measuring cuff becomes loose.

The "predetermined second pressure range" refers to, for example, a range of 10 mmHg to 15 mmHg.

There is a tendency that the Korotkoff sound level decreases as the winding strength of the blood pressure measuring cuff becomes loose, while the Korotkoff sound level increases as the winding strength of the blood pressure measuring cuff becomes tight. Here, for example, as disclosed in Patent Literature 3 (JP 5408142 B2), in the predetermined second pressure range (for example, a range of 10 mmHg to 15 mmHg) below the first pressure range, the second passage time required for the cuff pressure to pass through the second pressure range changes according to the cuff size and the winding strength. That is, under the condition set to a certain cuff size, the second passage time corresponds to the winding strength. Therefore, in the sphygmomanometer according to this embodiment, the amplification factor setting unit measures the second passage time required for the pressure of the blood pressure measuring cuff to pass through the second pressure range in the pressurization process of the blood pressure measuring cuff by the pressure device, and sets the amplification factor to be large as the second passage time becomes longer as the winding strength of the blood pressure measuring cuff becomes loose. Therefore, the change of the Korotkoff sound level depending on the winding strength of the blood pressure measuring cuff can be reliably reduced or eliminated. As a result, the blood pressure calculation unit can measure the blood pressure with higher accuracy.

In another aspect, a sphygmomanometer that measures a blood pressure by a Korotkoff sound generated by a site to be measured, the sphygmomanometer of the present disclosure comprises:

a blood pressure measuring cuff worn around the site to be measured;

a pressure device that supplies a fluid to the blood pressure measuring cuff to pressurize the blood pressure measuring cuff, or discharges a fluid from the blood pressure measuring cuff to depressurize the blood pressure measuring cuff;

a sound detection device that detects a sound generated by the site to be measured via the blood pressure measuring cuff;

an input unit that inputs size information indicating which cuff size the currently connected blood pressure measuring cuff has among a plurality of types of cuff sizes prepared in advance;

an amplification factor setting unit that variably sets an amplification factor for a Korotkoff sound component according to the size information input by the input unit; and a blood pressure calculation unit that receives an output of the sound detection device according to the sound from the blood pressure measuring cuff, amplifies a Korotkoff sound component included in the output with an amplification factor set by the amplification factor setting unit, and calculates a blood pressure of the site to be measured based on the amplified Korotkoff sound component in a pressurization process or a depressurization process by the pressure device.

In other words, the sphygmomanometer of the present disclosure includes the input unit that inputs the size information indicating which cuff size the currently connected blood pressure measuring cuff has among the plurality of types of cuff sizes prepared in advance, and the amplification factor setting unit variably sets an amplification factor for the Korotkoff sound component according to the size information input by the input unit instead of obtaining the first passage time.

In the sphygmomanometer of the present disclosure, the input unit inputs the size information indicating which cuff size the currently connected blood pressure measuring cuff has among the plurality of types of cuff sizes prepared in advance. Instead of obtaining the first passage time, the amplification factor setting unit variably sets an amplification factor for the Korotkoff sound component according to the size information input by the input unit. The blood pressure calculation unit receives the output of the sound detection device according to the sound from the blood pressure measuring cuff, amplifies the Korotkoff sound component included in the output with the amplification factor set by the amplification factor setting unit, and calculates the blood pressure of the site to be measured based on the amplified Korotkoff sound component in the pressurization process or the depressurization process by the pressure device. As a result, it is possible to reduce or eliminate the change of the Korotkoff sound level depending on the peripheral length (corresponding to the cuff size) of the site to be measured. Therefore, the blood pressure calculation unit can accurately measure the blood pressure.

As is clear from the above, according to the sphygmomanometer of the present disclosure, the change of the Korotkoff sound level depending on the peripheral length of the site to be measured can be reduced or eliminated, and the blood pressure can be accurately measured.

The above embodiments are illustrative, and various modifications can be made without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer that measures a blood pressure by a Korotkoff sound generated by a site to be measured, the sphygmomanometer comprising:

a blood pressure measuring cuff configured to be worn around the site to be measured, wherein the blood pressure measuring cuff includes:

an outer cloth extending in a longitudinal direction in a band shape and configured to surround the site to be measured;

a pressing fluid bag provided to extend along the longitudinal direction on a side of the outer cloth facing the site to be measured and configured to compress the site to be measured; and a sound acquisition fluid bag provided between the outer cloth and the pressing fluid bag in a thickness direction perpendicular to the outer cloth, and configured to acquire a sound from the site to be measured via the pressing fluid bag;

a pressure device that supplies a fluid to the blood pressure measuring cuff to pressurize the blood pressure measuring cuff, or discharges the fluid from the blood pressure measuring cuff to depressurize the blood pressure measuring cuff;

a microphone that detects a sound generated by the site to be measured via the blood pressure measuring cuff; and a processor, wherein the processor is configured to:

act as an amplification factor setting unit to measure a first passage time required for pressure of the blood pressure measuring cuff to pass through a predetermined first pressure range in a pressurization process of the blood pressure measuring cuff by the pressure device, and variably set an amplification factor for a Korotkoff sound component according to the first passage time; and act as a blood pressure calculation unit to receive an output of the microphone according to the sound from the blood pressure measuring cuff, amplify a Korotkoff sound component included in the output with the amplification factor set by the amplification factor setting unit, and calculate a blood pressure of the site to be measured based on the amplified Korotkoff sound component in the pressurization process or a depressurization process subsequent to the pressurization process.

2. The sphygmomanometer according to claim 1, wherein the sphygmomanometer further comprises:

a main body provided separately from the blood pressure measuring cuff and mounting the pressure device, the microphone, and the processor;

a first fluid pipe that connects the pressing fluid bag and the pressure device so as to be capable of flowing a fluid; and a second fluid pipe that is provided separately from the first fluid pipe and connects the sound acquisition fluid bag and the microphone so as to be capable of flowing a fluid.

3. The sphygmomanometer according to claim 1, wherein a length in a longitudinal direction of the blood pressure measuring cuff and/or the pressing fluid bag included in the blood pressure measuring cuff is variably set according to a peripheral length of the site to be measured, and when acting as the amplification factor setting unit, the processor is configured to set the amplification factor to be larger as the first passage time becomes longer in accordance with an increase in the length in the longitudinal direction and/or a width direction of the blood pressure measuring cuff and/or the pressing fluid bag.

4. The sphygmomanometer according to claim 1, wherein when acting as the amplification factor setting unit, the processor is configured to:

measure a second passage time required for the pressure of the blood pressure measuring cuff to pass through a predetermined second pressure range below the first pressure range in the pressurization process of the blood pressure measuring cuff by the pressure device; and set the amplification factor to be larger as the second passage time becomes longer in accordance with a winding strength of the blood pressure measuring cuff becoming looser.

* * * * *